(12) United States Patent
Chiu et al.

(10) Patent No.: US 11,367,528 B2
(45) Date of Patent: *Jun. 21, 2022

(54) PROACTIVE IMAGE-BASED INFUSION DEVICE DELIVERY ADJUSTMENTS

(71) Applicant: MEDTRONIC MINIMED, INC., Northridge, CA (US)

(72) Inventors: Chia-Hung Chiu, Pasadena, CA (US); Rebecca K. Gottlieb, Culver City, CA (US); Carol A. Jerome, Mission Hills, CA (US); Kenny J. Long, Simi Valley, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/081,942

(22) Filed: Oct. 27, 2020

(65) Prior Publication Data

US 2021/0065896 A1  Mar. 4, 2021

Related U.S. Application Data

(63) Continuation of application No. 16/403,451, filed on May 3, 2019, now Pat. No. 10,861,603.

(Continued)

(51) Int. Cl.
| | |
|---|---|
| *G16H 40/67* | (2018.01) |
| *G16H 40/63* | (2018.01) |
| *A61B 90/00* | (2016.01) |
| *A61M 5/172* | (2006.01) |
| *G06K 9/00* | (2022.01) |
| *G16H 20/30* | (2018.01) |

(Continued)

(52) U.S. Cl.
CPC ............. *G16H 40/67* (2018.01); *A61B 90/36* (2016.02); *A61M 5/1723* (2013.01); *G06T 19/006* (2013.01); *G06V 20/20* (2022.01); *G16H 20/17* (2018.01); *G16H 20/30* (2018.01); *G16H 20/60* (2018.01); *G16H 40/63* (2018.01); *A61B 2090/365* (2016.02); *A61M 2005/14208* (2013.01); *A61M 2205/3553* (2013.01)

(58) Field of Classification Search
CPC .............................. G16H 20/17; A61M 5/1723
USPC .......................................................... 604/65
See application file for complete search history.

(56) References Cited

U.S. PATENT DOCUMENTS

| | | |
|---|---|---|
| 4,562,751 A | 1/1986 | Nason et al. |
| 4,685,903 A | 8/1987 | Cable et al. |

(Continued)

*Primary Examiner* — Javid A Amini
(74) *Attorney, Agent, or Firm* — Carter, DeLuca & Farrell LLP

(57) ABSTRACT

Medical devices and related augmented reality systems and methods are provided. A method of operating an infusion device involves analyzing one or more images captured by an imaging device to identify image content indicative of an activity capable of influencing the physiological condition of the patient and in response to identifying the activity based at least in part on the one or more images, automatically adjusting delivery of the fluid to the patient based at least in part on the activity. An expected nutritional characteristic for a meal is determined based at least in part on the image content, and a delivery adjustment for delivering the fluid is determined based on the expected nutritional characteristic. A graphical indication of the delivery adjustment may also be provided using augmented reality.

20 Claims, 22 Drawing Sheets

Related U.S. Application Data

(60) Provisional application No. 62/791,196, filed on Jan. 11, 2019, provisional application No. 62/668,022, filed on May 7, 2018.

(51) Int. Cl.
  *G16H 20/60* (2018.01)
  *G06T 19/00* (2011.01)
  *G16H 20/17* (2018.01)
  *G06V 20/20* (2022.01)
  *A61M 5/142* (2006.01)

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,175,752 B1 | 1/2001 | Say et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,922,590 B1 | 7/2005 | Whitehurst |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,534,226 B2 | 5/2009 | Mernoe et al. |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,199 B2 | 2/2011 | Mhatre et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,981,102 B2 | 7/2011 | Patel et al. |
| 7,985,330 B2 | 7/2011 | Wang et al. |
| 8,024,201 B2 | 9/2011 | Brown |
| 8,100,852 B2 | 1/2012 | Moberg et al. |
| 8,105,279 B2 | 1/2012 | Mernoe et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,394 B2 | 6/2012 | Estes et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,287,514 B2 | 10/2012 | Miller et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,454,557 B1 | 6/2013 | Qi et al. |
| 8,454,581 B2 | 6/2013 | Estes et al. |
| 8,474,332 B2 | 7/2013 | Bente, IV |
| 8,480,649 B2 * | 7/2013 | Yodfat .................. G16H 10/40 604/504 |
| 8,674,288 B2 | 3/2014 | Hanson et al. |
| 9,427,523 B2 | 8/2016 | Qi et al. |
| 9,457,141 B2 | 10/2016 | Smith et al. |
| 9,561,324 B2 | 2/2017 | Estes |
| 9,629,901 B2 | 4/2017 | Estes |
| 9,744,298 B2 * | 8/2017 | Prince .................. G16H 20/17 |
| D809,134 S | 1/2018 | Crothall |
| 9,878,097 B2 | 1/2018 | Estes |
| 9,919,096 B2 | 3/2018 | Brewer et al. |
| 10,016,169 B2 * | 7/2018 | Meador ................ A61B 5/0816 |
| 10,137,246 B2 | 11/2018 | Estes et al. |
| 10,424,121 B1 | 9/2019 | Melinek et al. |
| 10,449,294 B1 | 10/2019 | Estes |
| 10,505,910 B2 * | 12/2019 | Gegner .................. G16H 40/67 |
| 10,569,015 B2 | 2/2020 | Estes |
| 10,661,007 B2 | 5/2020 | Estes |
| 10,661,008 B2 | 5/2020 | Brewer et al. |
| 10,861,603 B2 * | 12/2020 | Chiu .................... G06T 19/006 |
| 2006/0031094 A1 | 2/2006 | Cohen et al. |
| 2007/0123819 A1 | 5/2007 | Mernoe et al. |
| 2009/0299301 A1 | 12/2009 | Gottlieb et al. |
| 2009/0326722 A1 | 12/2009 | Pohlman et al. |
| 2010/0094251 A1 | 4/2010 | Estes |
| 2010/0160861 A1 | 6/2010 | Causey, III et al. |
| 2011/0106050 A1 * | 5/2011 | Yodfat ................ A61M 5/1723 604/504 |
| 2011/0190595 A1 | 8/2011 | Bennett et al. |
| 2012/0006100 A1 | 1/2012 | Gottlieb et al. |
| 2014/0066889 A1 | 3/2014 | Grosman et al. |

(56) References Cited

U.S. PATENT DOCUMENTS

| | | | |
|---|---|---|---|
| 2014/0219525 A1* | 8/2014 | Eder | G16H 50/30 |
| | | | 382/128 |
| 2014/0277249 A1 | 9/2014 | Connor | |
| 2015/0228062 A1 | 8/2015 | Joshi et al. | |
| 2015/0332620 A1 | 11/2015 | Sako et al. | |
| 2016/0012749 A1 | 1/2016 | Connor | |
| 2017/0039423 A1* | 2/2017 | Cork | G02B 27/0172 |
| 2018/0169333 A1 | 6/2018 | Grosman et al. | |
| 2018/0242920 A1* | 8/2018 | Hresko | G06K 9/00718 |
| 2018/0271455 A1 | 9/2018 | Zhong et al. | |
| 2018/0345082 A1 | 12/2018 | Kimura et al. | |
| 2019/0340434 A1* | 11/2019 | Chiu | G16H 20/17 |
| 2019/0341149 A1* | 11/2019 | Chiu | G16H 20/30 |

* cited by examiner

PROACTIVE IMAGE-BASED INFUSION DEVICE DELIVERY ADJUSTMENTS

CROSS-REFERENCE TO RELATED APPLICATION(S)

This application is a continuation of U.S. patent application Ser. No. 16/403,451, filed May 3, 2019, which claims the benefit of U.S. Provisional Patent Application Ser. No. 62/791,196, filed Jan. 11, 2019, and U.S. Provisional Patent Application Ser. No. 62/668,022, filed May 7, 2018, the entire contents of which are incorporated by reference herein.

This application is also related to U.S. patent application Ser. No. 16/403,453 and U.S. patent application Ser. No. 16/403,454, both filed May 3, 2019.

TECHNICAL FIELD

Embodiments of the subject matter described herein relate generally to medical devices, and more particularly, embodiments of the subject matter relate to using augmented reality to improve patient experience or outcome.

BACKGROUND

The use of portable medical devices, such as infusion pump devices, continuous glucose monitors, and the like, has been increasing to improve the control or management of a patient's condition. Additionally, modern devices may incorporate or support any number of potential features as well as utilizing various user interface(s), which may be unique to a particular device. However, for some users, increased device complexity can be perceived as confusing, time consuming, or inconvenient. Accordingly, it is desirable to provide methods and systems that facilitate maximizing device performance to achieve better patient outcomes while also improving user experience by reducing patient burdens. Furthermore, other desirable features and characteristics will become apparent from the subsequent detailed description and the appended claims, taken in conjunction with the accompanying drawings and this background.

BRIEF SUMMARY

Medical devices and related systems and operating methods are provided. An embodiment of a method of facilitating operation of a medical device involves identifying, by a computing device, a current state of a user interface of the medical device based at least in part on a portion of the medical device captured by an imaging device associated with the computing device, generating, by the computing device, guidance information pertaining to the current state of the user interface, and presenting, by the computing device, a guidance overlay including the guidance information pertaining to the current state of the user interface.

In another embodiment, a method of providing guidance pertaining to a display associated with a medical device, such as an infusion device, involves obtaining, from an imaging device, one or more images capturing at least a portion of the display, identifying, based on the one or more images, a current graphical user interface (GUI) display presented on the display from among a plurality of GUI displays associated with the infusion device, identifying a user objective, generating, by a computing device, guidance information pertaining to the current GUI display based on the user objective, and providing a guidance overlay including the guidance information pertaining to the current GUI display, wherein the guidance overlay visually overlies at least a portion of the infusion device.

In yet another embodiment, an apparatus for an electronic device is provided. The electronic device includes an imaging device and a display having displayed thereon an augmented reality graphical user interface (GUI) display including a guidance overlay, wherein the guidance overlay visually overlies at least a portion of a medical device, the guidance overlay includes guidance information pertaining to a current state of a user interface of the medical device determined based at least in part one or more images captured by the imaging device, and the one or more images include at least some of the user interface of the medical device.

In another embodiment, a method of providing guidance to a patient using an electronic device having an imaging device associated therewith is provided. The method involves analyzing one or more images captured by the imaging device to identify image content indicative of a potential activity for the patient, determining, by a control system associated with the electronic device, one or more attributes for the potential activity, determining, by the control system, a predicted physiological response by the patient to the potential activity based at least in part on the one or more attributes, and providing, on a display associated with the electronic device, an augmented reality graphical user interface including a graphical indication influenced by the predicted physiological response.

In yet another embodiment, a method of providing guidance to a patient using an electronic device having an imaging device associated therewith involves obtaining an image of a meal using the imaging device, determining, by a control system associated with the electronic device, an estimated carbohydrate amount for the meal based at least in part on the image, determining, by the control system, a predicted physiological response by the patient to the meal based at least in part on the estimated carbohydrate amount, and providing, on a display associated with the electronic device, an augmented reality graphical user interface including a graphical indication influenced by the predicted physiological response.

In another embodiment, an apparatus for an electronic device having an imaging device and a display having displayed thereon an augmented reality graphical user interface (GUI) display is provided. The augmented reality GUI display includes a guidance overlay, wherein the guidance overlay visually overlies at least a portion of content captured by the imaging device, the content is indicative of a potential activity capable of influencing a physiological condition of a patient, the guidance overlay includes guidance information influenced by a predicted physiological response by the patient to the potential activity, and the predicted physiological response is determined based on recent data associated with the patient and one or more attributes for the potential activity.

In another embodiment, a method of operating an infusion device capable of delivering fluid to a patient is provided. The method involves analyzing one or more images captured by an imaging device to identify image content indicative of an activity capable of influencing the physiological condition of the patient and in response to identifying the activity based at least in part on the one or more images, automatically adjusting delivery of the fluid to the patient based at least in part on the activity.

In one embodiment, a method of operating an infusion device capable of delivering fluid to a patient involves obtaining an image of a meal captured by an imaging device, determining, by a control system associated with the infusion device, an expected nutritional characteristic for the meal based at least in part on the image, determining, by the control system, a delivery adjustment for delivering the fluid based on the expected nutritional characteristic, and providing, on a display, an augmented reality graphical user interface including an overlay comprising a graphical indication of the delivery adjustment.

In yet another embodiment, an apparatus for an electronic device is provided. The electronic device includes an imaging device and a display having displayed thereon an augmented reality graphical user interface (GUI) display including a guidance overlay, wherein the guidance overlay visually overlies at least a portion of meal content captured by the imaging device, the guidance overlay includes guidance information influenced by a predicted physiological response by a patient to the meal content, and the guidance overlay includes graphical indication of a delivery adjustment to an infusion device associated with the patient, wherein the delivery adjustment is determined based at least in part on the meal content captured by the imaging device and the delivery adjustment is influenced by the predicted physiological response by the patient to the meal content.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
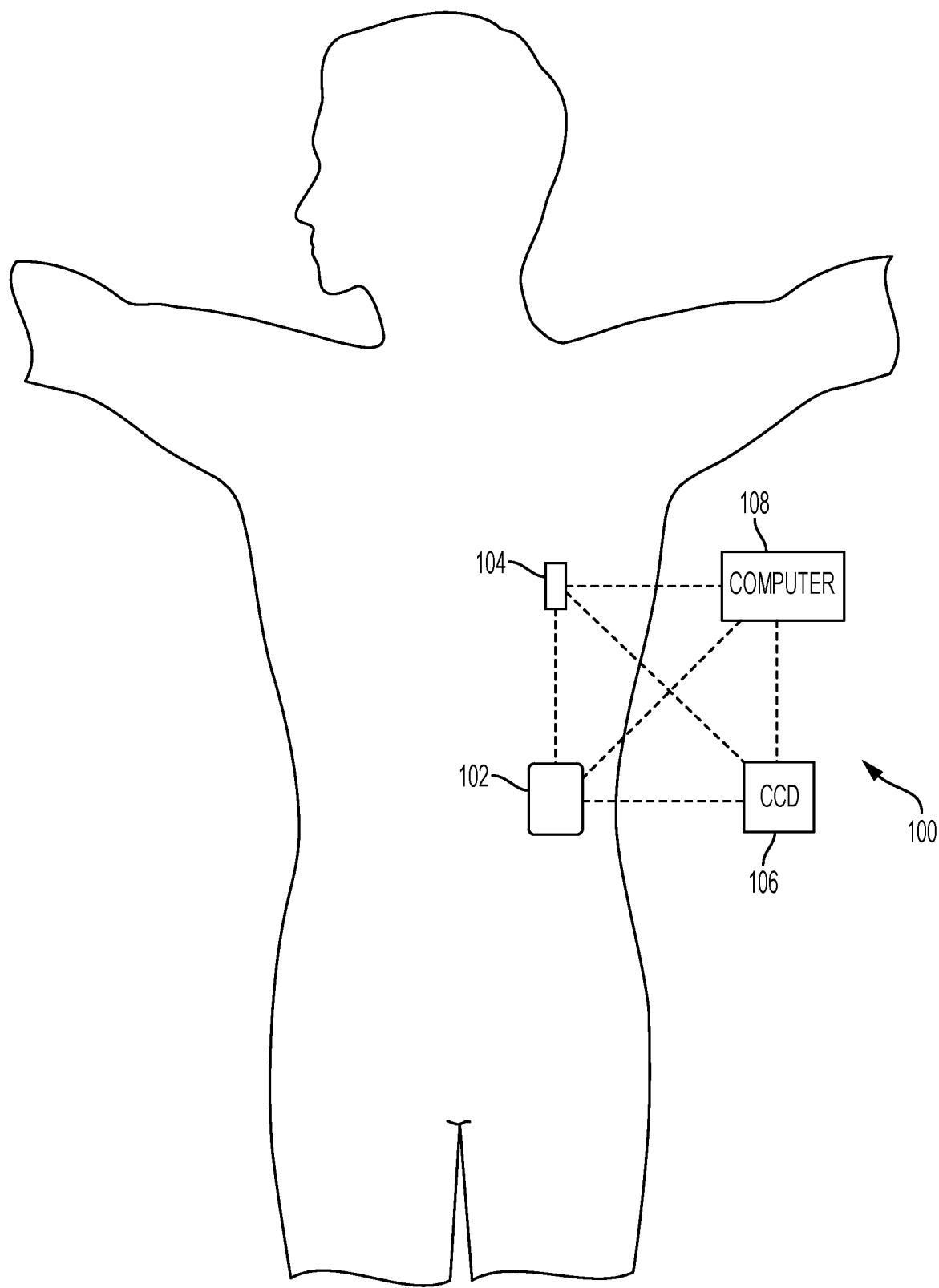
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein are implemented in conjunction with medical devices, such as portable electronic medical devices. Although many different applications are possible, the following description focuses on embodiments that incorporate a fluid infusion device (or infusion pump) as part of an infusion system deployment. That said, the subject matter described herein is not limited to infusion devices (or any particular configuration or realization thereof) and may be implemented in an equivalent manner in the context of other medical devices, such as continuous glucose monitoring (CGM) devices, injection pens (e.g., smart injection pens), and the like. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference. That said, the subject matter described herein can be utilized more generally in the context of overall diabetes management or other physiological conditions independent of or without the use of an infusion device or other medical device (e.g., when oral medication is utilized), and the subject matter described herein is not limited to any particular type of medication.

Generally, a fluid infusion device includes a motor or other actuation arrangement that is operable to linearly displace a plunger (or stopper) of a reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Exemplary embodiments of the subject matter described herein generally relate to utilizing augmented reality and other image processing to assist or improve operations of medical devices in a convenient manner that reduces patient burdens. For example, as described in greater detail below in the context of FIGS. 8-17, in one or more exemplary embodiments, augmented reality is utilized to interactively provide visually overlaid guidance information to help facilitate the configuration or operation of various features of a medical device. In this regard, a camera or other imaging device may be utilized to capture or otherwise obtain an image of the medical device, which, in turn, is analyzed to identify the current state of a user interface of the medical device, such as, for example, the graphical user interface (GUI) currently displayed on a display of the medical device, a current selection or position of a user input element on the display, and the like. Based on the current user interface status information, guidance information is determined and presented or otherwise provided on a display in a manner that overlies the medical device, and thereby enables review of the guidance information while concurrently viewing at least a portion of the medical device GUI. The patient or other user may then concurrently view the guidance information for accomplishing a particular objective in the foreground while interacting with the medical device in the background, thereby improving the user experience by allowing cross-referencing the user inputs with the guidance information in an intuitive manner without diverting the head or eyes of the user. Additionally, some embodiments could employ text-to-speech functionality to provide guidance information or other feedback in an auditory manner. For example, text-to-speech could be employed to read back text depicted on the captured medical device GUI to support visually impaired patients or other users who prefer auditory feedback.

Additionally, as described in greater detail below in the context of FIGS. 18-20, in one or more exemplary embodiments, overlaid guidance information or other graphical indicia are provided based on a patient's predicted physiological response to a portion of the content in a captured image. For example, food, beverages, or other consumable items (or indicia thereof) may be identified within a captured image. Estimated carbohydrate amounts or other attributes (e.g., fiber, fat, protein, and/or the like) associated with the captured consumable(s) may be input or otherwise provided to one or more prediction models to calculate or otherwise determine a predicted physiological response by the patient to consumption of at least some of the consumable items captured by the imaging device. Based on the predicted physiological response, graphical overlays may be provided proximate to the consumable items that indicate, to the patient, his or her predicted physiological response to consuming those items, or provide guidance or other recommendations to the patient regarding consuming those items (e.g., a recommended portion size, recommendations to abstain from consumption, or the like). In this manner, the guidance overlays may encourage or motivate the patient towards behavior that improves the patient's physiological condition (or the management thereof) or otherwise achieves a better outcome. In a similar manner, content in a captured image may be analyzed to identify items or other indicia associated with exercise (e.g., a treadmill, a gym, or the like), which, in turn may be utilized to estimate or otherwise determine a predicted physiological response to exercise and provide graphical overlays that provide suggestions, recommendations, or other guidance for exercise to improve the patient's physiological condition.

Figure 21:
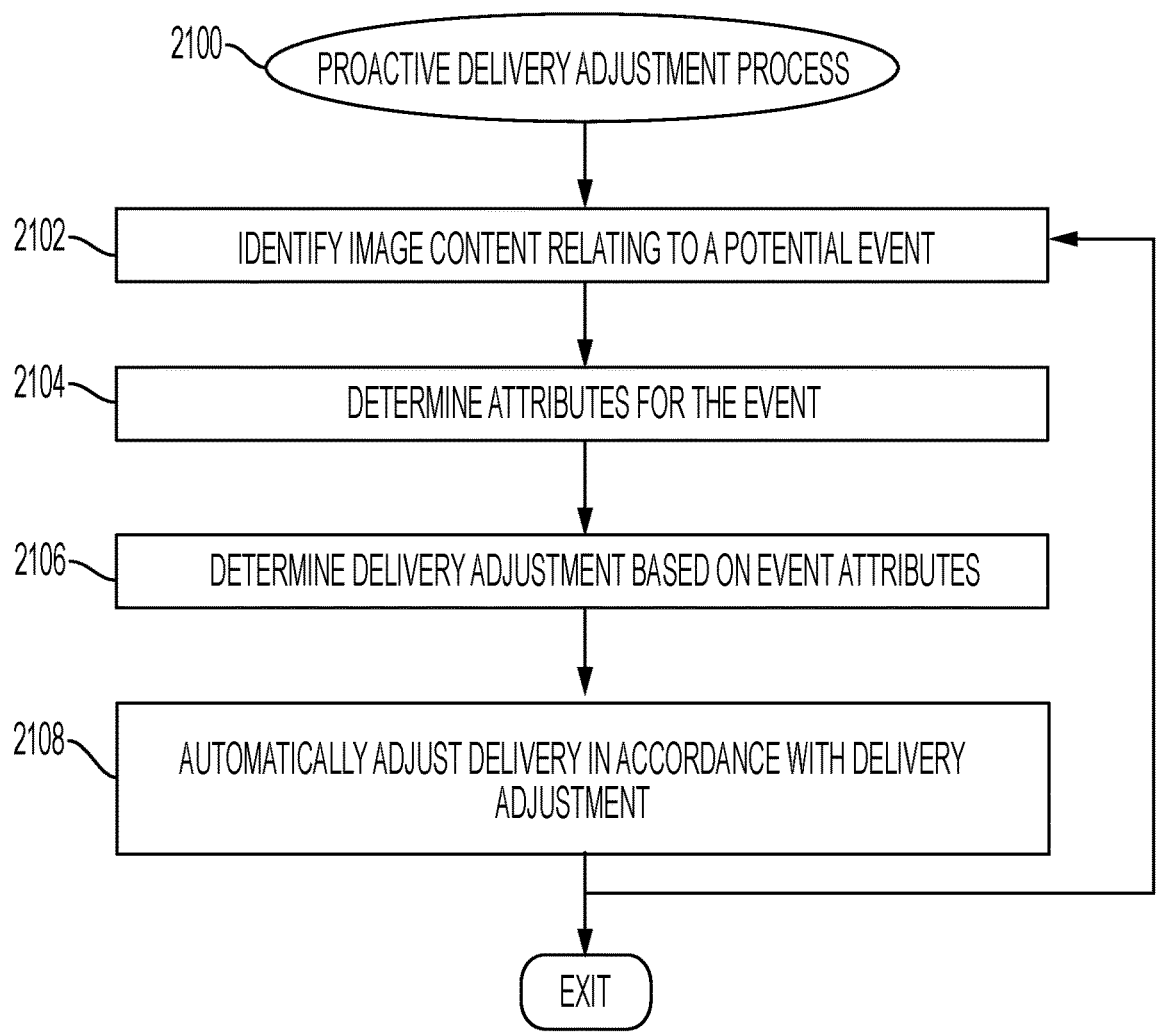
FIG. 21 is a flow diagram of an exemplary proactive delivery adjustment process in one or more exemplary embodiments.
Figure 22:
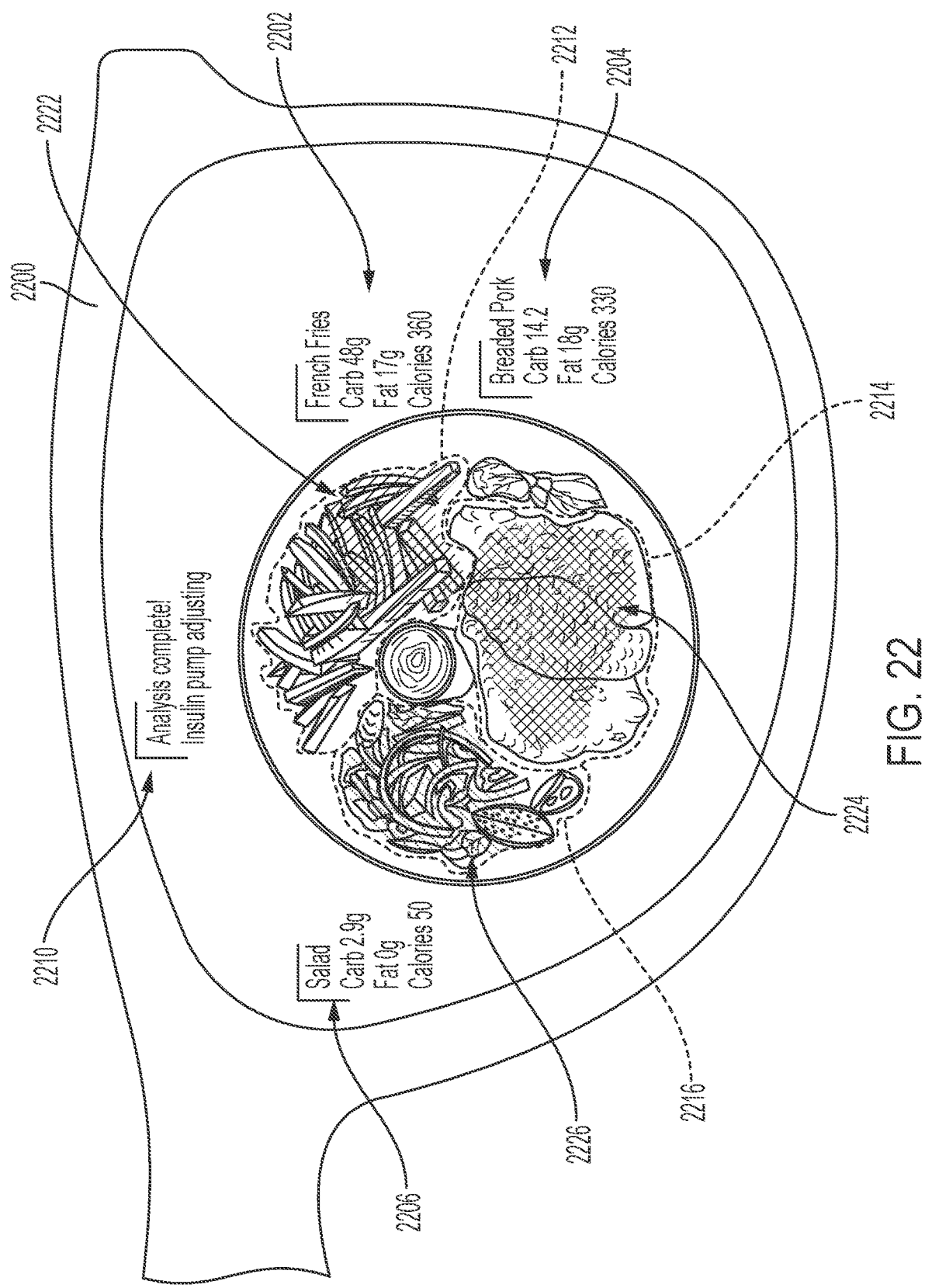
FIG. 22 is an exemplary augmented reality GUI displays suitable for presentation by an electronic device in connection with the proactive delivery adjustment process of FIG. 21.

As described in the context of FIGS. 21-22, in one or more exemplary embodiments, captured images are also utilized to automatically and proactively adjust delivery control parameters or fluid delivery to account for the content of the captured images. For example, when a patient is about to begin consuming a meal, an image of the meal may be analyzed to identify the type of food being consumed, the nutritional characteristics or other content of the meal, the estimated portion size, and/or the like. The estimated portion size, nutritional characteristics or food type, and other attributes identified based on the captured image may be utilized to calculate or otherwise determine an estimated amount of carbohydrates expected to be consumed by the patient. Based on the estimated amount of carbohydrates, fat, protein, fiber, and/or other nutritional attributes of the current meal expected to be consumed by the patient, one or more control parameters of an infusion device may be automatically adjusted to proactively account for the probable metabolic or pharmacokinetic response to the meal. Additionally, or alternatively, one or more bolus amounts of insulin to be delivered may be calculated or otherwise determined based on the estimated carbohydrate amount. A confirmation graphical overlay may be provided that confirms or otherwise informs the patient of the proactive delivery adjustments that were automatically configured in response to a captured image. Additionally, overlaid information may provide graphical indicia that provide feedback to the patient regarding the results of the analysis of the captured image, such as, for example, indication of the estimated amounts of carbohydrates, fat, protein, fiber, and/or other nutritional attributes associated with the meal.

In one or more embodiments, the control parameters or other delivery adjustments may be performed dynamically in real-time in response to changes in the captured imagery over time. For example, successive images may be analyzed to identify or otherwise determine the amount of the meal that has been consumed over a given duration of time, which in turn, may be utilized to alter the delivery adjustments based on deviations between the patient's actual meal consumption relative to the initial prediction of the patient's expected consumption. Thus, when it appears that the patient did not or will not consume the entire meal after adjusting one or more control parameters to increase responsiveness of the fluid delivery to mitigate potential postprandial hyperglycemia, the control parameter(s) may be adjusted to decrease the responsiveness of the fluid delivery and account for the reduced likelihood of hyperglycemia based on reduced consumption by the patient. In a similar manner, content in a captured image may be analyzed to identify items or other indicia associated with exercise, which, in turn may be utilized to automatically adjust control parameters to proactively account for a predicted physiological response to exercise and dynamically revert the control parameters when the patient has ceased exercising.

Infusion System Overview

FIG. 1 depicts one exemplary embodiment of an infusion system 100 that includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589, 229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
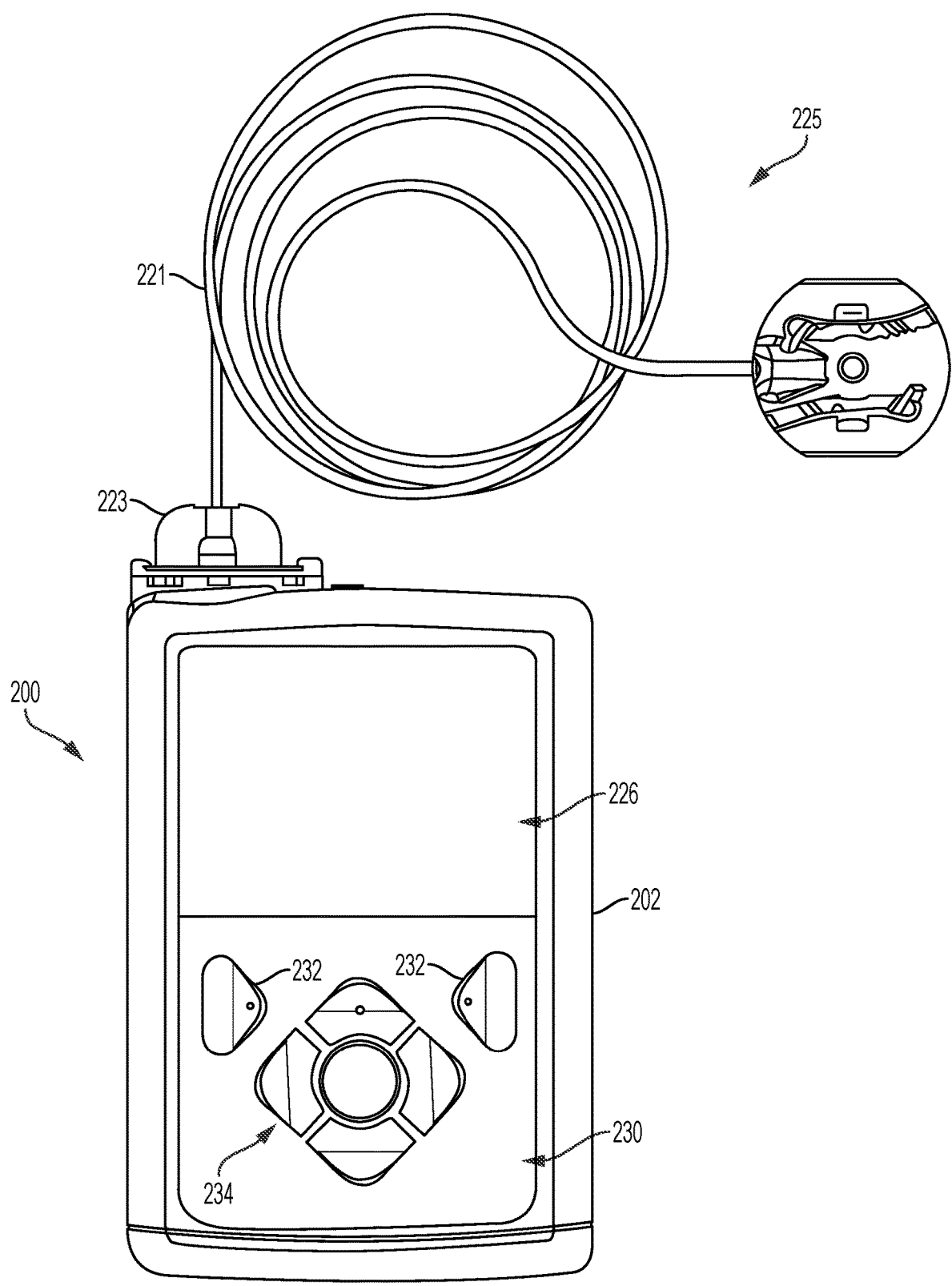
FIG. 2 depicts a plan view of an exemplary embodiment of a fluid infusion device suitable for use in the infusion system of FIG. 1 in one or more embodiments.
Figure 3:
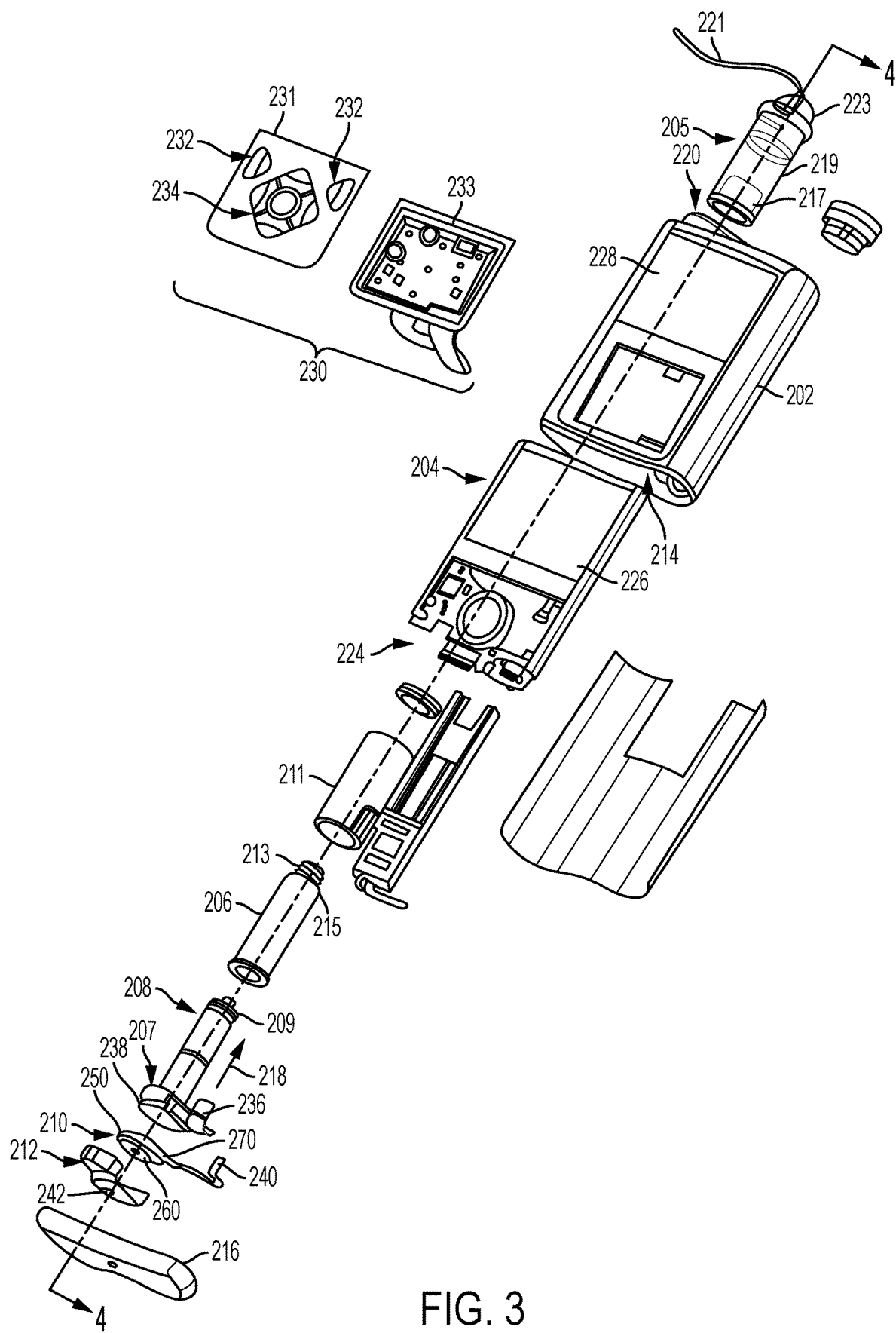
FIG. 3 is an exploded perspective view of the fluid infusion device of FIG. 2.

FIGS. 2-3 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-3 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIG. 3, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIG. 3, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

In some embodiments, the drive screw 209 mates with threads internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads on the plunger 217 of the reservoir 205, as described in detail in U.S. Pat. Nos. 6,248,093 and 6,485,465, which are incorporated by reference herein.

The electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 4. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-3, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIG. 3, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 4:
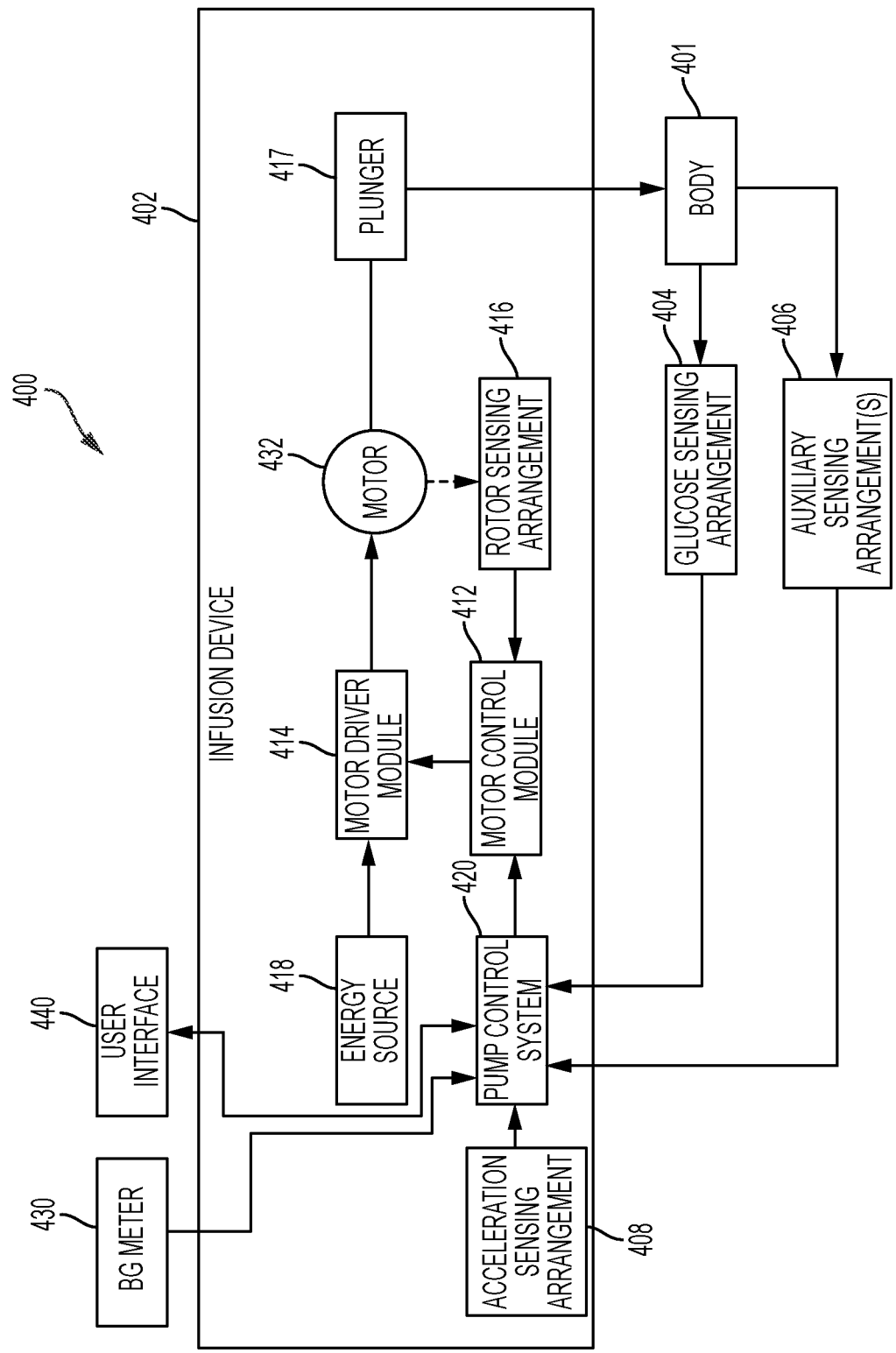
FIG. 4 is a block diagram of an exemplary infusion system suitable for use with a fluid infusion device in one or more embodiments.

FIG. 4 depicts an exemplary embodiment of an infusion system 400 suitable for use with an infusion device 402, such as any one of the infusion devices 102, 200 described above. The infusion system 400 is capable of controlling or otherwise regulating a physiological condition in the body 401 of a patient to a desired (or target) value or otherwise maintain the condition within a range of acceptable values in an automated or autonomous manner. In one or more exemplary embodiments, the condition being regulated is sensed, detected, measured or otherwise quantified by a sensing arrangement 404 (e.g., sensing arrangement 404) communicatively coupled to the infusion device 402. However, it should be noted that in alternative embodiments, the condition being regulated by the infusion system 400 may be correlative to the measured values obtained by the sensing arrangement 404. That said, for clarity and purposes of explanation, the subject matter may be described herein in the context of the sensing arrangement 404 being realized as a glucose sensing arrangement that senses, detects, measures or otherwise quantifies the patient's glucose level, which is being regulated in the body 401 of the patient by the infusion system 400.

In exemplary embodiments, the sensing arrangement 404 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 401 of the patient. The output electrical signals are filtered or otherwise processed to obtain a measurement value indicative of the patient's interstitial fluid glucose level. In exemplary embodiments, a blood glucose meter 430, such as a finger stick device, is utilized to directly sense, detect, measure or otherwise quantify the blood glucose in the body 401 of the patient. In this regard, the blood glucose meter 430 outputs or otherwise provides a measured blood glucose value that may be utilized as a reference measurement for calibrating the sensing arrangement 404 and converting a measurement value indicative of the patient's interstitial fluid glucose level into a corresponding calibrated blood glucose value. For purposes of explanation, the calibrated blood glucose value calculated based on the electrical signals output by the sensing element(s) of the sensing arrangement 404 may alternatively be referred to herein as the sensor glucose value, the sensed glucose value, or variants thereof.

In exemplary embodiments, the infusion system 400 also includes one or more additional sensing arrangements 406, 408 configured to sense, detect, measure or otherwise quantify a characteristic of the body 401 of the patient that is indicative of a condition in the body 401 of the patient. In this regard, in addition to the glucose sensing arrangement 404, one or more auxiliary sensing arrangements 406 may be worn, carried, or otherwise associated with the body 401 of the patient to measure characteristics or conditions of the patient (or the patient's activity) that may influence the patient's glucose levels or insulin sensitivity. For example, a heart rate sensing arrangement 406 could be worn on or otherwise associated with the patient's body 401 to sense, detect, measure or otherwise quantify the patient's heart rate, which, in turn, may be indicative of exercise (and the intensity thereof) that is likely to influence the patient's glucose levels or insulin response in the body 401. In yet another embodiment, another invasive, interstitial, or subcutaneous sensing arrangement 406 may be inserted into the body 401 of the patient to obtain measurements of another physiological condition that may be indicative of exercise (and the intensity thereof), such as, for example, a lactate sensor, a ketone sensor, or the like. Depending on the embodiment, the auxiliary sensing arrangement(s) 406 could be realized as a standalone component worn by the patient, or alternatively, the auxiliary sensing arrangement(s) 406 may be integrated with the infusion device 402 or the glucose sensing arrangement 404.

The illustrated infusion system 400 also includes an acceleration sensing arrangement 408 (or accelerometer) that may be worn on or otherwise associated with the patient's body 401 to sense, detect, measure or otherwise quantify an acceleration of the patient's body 401, which, in turn, may be indicative of exercise or some other condition in the body 401 that is likely to influence the patient's insulin response. While the acceleration sensing arrangement 408 is depicted as being integrated into the infusion device 402 in FIG. 4, in alternative embodiments, the acceleration sensing arrangement 408 may be integrated with another sensing arrangement 404, 406 on the body 401 of the patient, or the acceleration sensing arrangement 408 may be realized as a separate standalone component that is worn by the patient.

In the illustrated embodiment, the pump control system 420 generally represents the electronics and other components of the infusion device 402 that control operation of the fluid infusion device 402 according to a desired infusion delivery program in a manner that is influenced by the sensed glucose value indicating the current glucose level in the body 401 of the patient. For example, to support a closed-loop operating mode, the pump control system 420 maintains, receives, or otherwise obtains a target or commanded glucose value, and automatically generates or otherwise determines dosage commands for operating an actuation arrangement, such as a motor 432, to displace the plunger 417 and deliver insulin to the body 401 of the patient based on the difference between the sensed glucose value and the target glucose value. In other operating modes, the pump control system 420 may generate or otherwise determine dosage commands configured to maintain the sensed glucose value below an upper glucose limit, above a lower glucose limit, or otherwise within a desired range of glucose values. In practice, the infusion device 402 may store or otherwise maintain the target value, upper and/or lower glucose limit(s), insulin delivery limit(s), and/or other glucose threshold value(s) in a data storage element accessible to the pump control system 420. As described in greater detail, in one or more exemplary embodiments, the pump control system 420 automatically adjusts or adapts one or more parameters or other control information used to generate commands for operating the motor 432 in a manner that accounts for a likely change in the patient's glucose level or insulin response resulting from a meal, exercise, or other activity.

Still referring to FIG. 4, the target glucose value and other threshold glucose values utilized by the pump control system 420 may be received from an external component (e.g., CCD 106 and/or computing device 108) or be input by a patient via a user interface element 440 associated with the infusion device 402. In practice, the one or more user interface element(s) 440 associated with the infusion device 402 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 440 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the patient. It should be noted that although FIG. 4 depicts the user interface element(s) 440 as being separate from the infusion device 402, in practice, one or more of the user interface element(s) 440 may be integrated with the infusion device 402. Furthermore, in some embodiments, one or more user interface element(s) 440 are integrated with the sensing arrangement 404 in addition to and/or in alternative to the user interface element(s) 440 integrated with the infusion device 402. The user interface element(s) 440 may be manipulated by the patient to operate the infusion device 402 to deliver correction boluses, adjust target and/or threshold values, modify the delivery control scheme or operating mode, and the like, as desired.

Still referring to FIG. 4, in the illustrated embodiment, the infusion device 402 includes a motor control module 412 coupled to a motor 432 (e.g., motor assembly 207) that is operable to displace a plunger 417 (e.g., plunger 217) in a reservoir (e.g., reservoir 205) and provide a desired amount of fluid to the body 401 of a patient. In this regard, displacement of the plunger 417 results in the delivery of a fluid, such as insulin, that is capable of influencing the patient's physiological condition to the body 401 of the patient via a fluid delivery path (e.g., via tubing 221 of an infusion set 225). A motor driver module 414 is coupled between an energy source 418 and the motor 432. The motor control module 412 is coupled to the motor driver module 414, and the motor control module 412 generates or otherwise provides command signals that operate the motor driver module 414 to provide current (or power) from the energy source 418 to the motor 432 to displace the plunger 417 in response to receiving, from a pump control system 420, a dosage command indicative of the desired amount of fluid to be delivered.

In exemplary embodiments, the energy source 418 is realized as a battery housed within the infusion device 402 (e.g., within housing 202) that provides direct current (DC) power. In this regard, the motor driver module 414 generally represents the combination of circuitry, hardware and/or other electrical components configured to convert or otherwise transfer DC power provided by the energy source 418 into alternating electrical signals applied to respective phases of the stator windings of the motor 432 that result in current flowing through the stator windings that generates a stator magnetic field and causes the rotor of the motor 432 to rotate. The motor control module 412 is configured to receive or otherwise obtain a commanded dosage from the pump control system 420, convert the commanded dosage to a commanded translational displacement of the plunger 417, and command, signal, or otherwise operate the motor driver module 414 to cause the rotor of the motor 432 to rotate by an amount that produces the commanded translational displacement of the plunger 417. For example, the motor control module 412 may determine an amount of rotation of the rotor required to produce translational displacement of the plunger 417 that achieves the commanded dosage received from the pump control system 420. Based on the current rotational position (or orientation) of the rotor with respect to the stator that is indicated by the output of the rotor sensing arrangement 416, the motor control module 412 determines the appropriate sequence of alternating electrical signals to be applied to the respective phases of the stator windings that should rotate the rotor by the determined amount of rotation from its current position (or orientation). In embodiments where the motor 432 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 412 operates the motor driver module 414 to apply the determined alternating electrical signals (e.g., the command signals) to the stator windings of the motor 432 to achieve the desired delivery of fluid to the patient.

When the motor control module 412 is operating the motor driver module 414, current flows from the energy source 418 through the stator windings of the motor 432 to produce a stator magnetic field that interacts with the rotor magnetic field. In some embodiments, after the motor control module 412 operates the motor driver module 414 and/or motor 432 to achieve the commanded dosage, the motor control module 412 ceases operating the motor driver module 414 and/or motor 432 until a subsequent dosage command is received. In this regard, the motor driver module 414 and the motor 432 enter an idle state during which the motor driver module 414 effectively disconnects or isolates the stator windings of the motor 432 from the energy source 418. In other words, current does not flow from the energy source 418 through the stator windings of the motor 432 when the motor 432 is idle, and thus, the motor 432 does not consume power from the energy source 418 in the idle state, thereby improving efficiency.

Depending on the embodiment, the motor control module 412 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 412 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 412. The computer-executable programming instructions, when read and executed by the motor control module 412, cause the motor control module 412 to perform or otherwise support the tasks, operations, functions, and processes described herein.

It should be appreciated that FIG. 4 is a simplified representation of the infusion device 402 for purposes of explanation and is not intended to limit the subject matter described herein in any way. In this regard, depending on the embodiment, some features and/or functionality of the sensing arrangement 404 may implemented by or otherwise integrated into the pump control system 420, or vice versa. Similarly, in practice, the features and/or functionality of the motor control module 412 may implemented by or otherwise integrated into the pump control system 420, or vice versa. Furthermore, the features and/or functionality of the pump control system 420 may be implemented by control electronics 224 located in the fluid infusion device 402, while in alternative embodiments, the pump control system 420 may be implemented by a remote computing device that is physically distinct and/or separate from the infusion device 402, such as, for example, the CCD 106 or the computing device 108.

Figure 5:
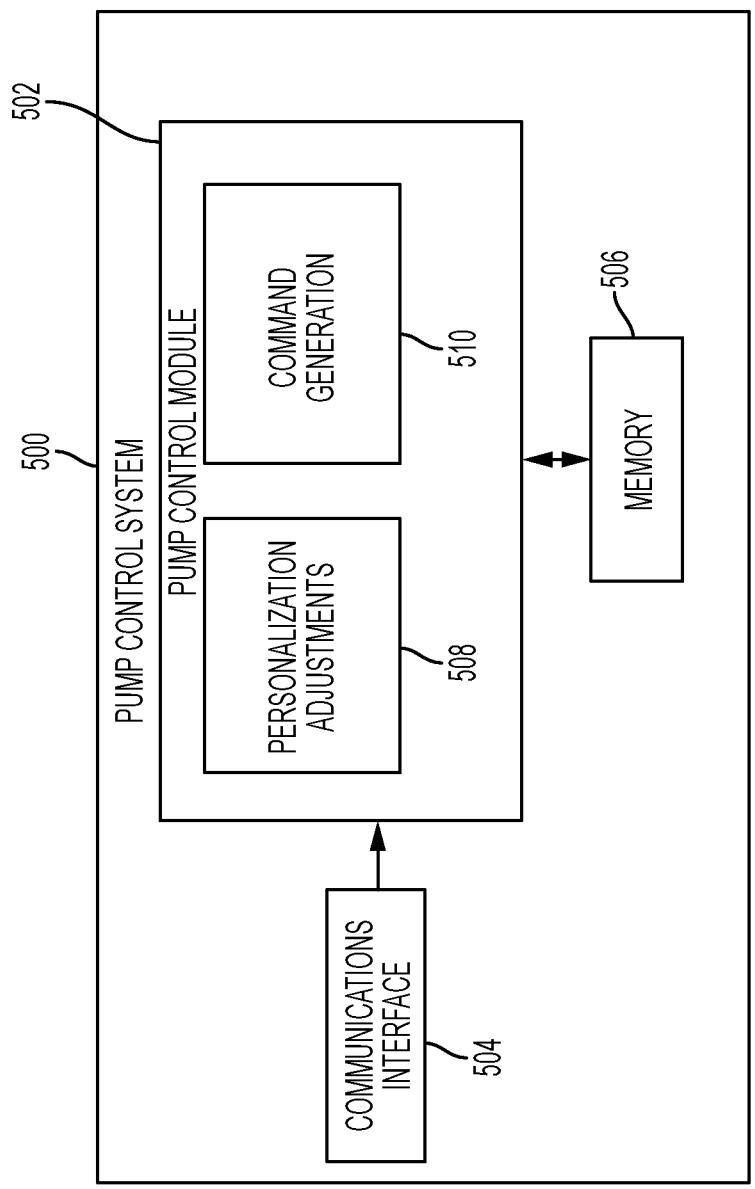
FIG. 5 is a block diagram of an exemplary pump control system suitable for use in the infusion device in the infusion system of FIG. 4 in one or more embodiments.

FIG. 5 depicts an exemplary embodiment of a pump control system 500 suitable for use as the pump control system 420 in FIG. 4 in accordance with one or more embodiments. The illustrated pump control system 500 includes, without limitation, a pump control module 502, a communications interface 504, and a data storage element (or memory) 506. The pump control module 502 is coupled to the communications interface 504 and the memory 506, and the pump control module 502 is suitably configured to support the operations, tasks, and/or processes described herein. In various embodiments, the pump control module 502 is also coupled to one or more user interface elements (e.g., user interface 230, 440) for receiving user inputs (e.g., target glucose values or other glucose thresholds) and providing notifications, alerts, or other therapy information to the patient.

The communications interface 504 generally represents the hardware, circuitry, logic, firmware and/or other components of the pump control system 500 that are coupled to the pump control module 502 and configured to support communications between the pump control system 500 and the various sensing arrangements 404, 406, 408. In this regard, the communications interface 504 may include or otherwise be coupled to one or more transceiver modules capable of supporting wireless communications between the pump control system 420, 500 and the sensing arrangement 404, 406, 408. For example, the communications interface 504 may be utilized to receive sensor measurement values or other measurement data from each sensing arrangement 404, 406, 408 in an infusion system 400. In other embodiments, the communications interface 504 may be configured to support wired communications to/from the sensing arrangement(s) 404, 406, 408. In various embodiments, the communications interface 504 may also support communications with another electronic device (e.g., CCD 106 and/or computer 108) in an infusion system (e.g., to upload sensor measurement values to a server or other computing device, receive control information from a server or other computing device, and the like).

The pump control module 502 generally represents the hardware, circuitry, logic, firmware and/or other component of the pump control system 500 that is coupled to the communications interface 504 and configured to determine dosage commands for operating the motor 432 to deliver fluid to the body 401 based on measurement data received from the sensing arrangements 404, 406, 408 and perform various additional tasks, operations, functions and/or operations described herein. For example, in exemplary embodiments, pump control module 502 implements or otherwise executes a command generation application 510 that supports one or more autonomous operating modes and calculates or otherwise determines dosage commands for operating the motor 432 of the infusion device 402 in an autonomous operating mode based at least in part on a current measurement value for a condition in the body 401 of the patient. For example, in a closed-loop operating mode, the command generation application 510 may determine a dosage command for operating the motor 432 to deliver insulin to the body 401 of the patient based at least in part on the current glucose measurement value most recently received from the sensing arrangement 404 to regulate the patient's blood glucose level to a target reference glucose value. Additionally, the command generation application 510 may generate dosage commands for boluses that are manually-initiated or otherwise instructed by a patient via a user interface element.

In exemplary embodiments, the pump control module 502 also implements or otherwise executes a personalization application 508 that is cooperatively configured to interact with the command generation application 510 to support adjusting dosage commands or control information dictating the manner in which dosage commands are generated in a personalized, patient-specific manner. In this regard, in some embodiments, based on correlations between current or recent measurement data and the current operational context relative to historical data associated with the patient, the personalization application 508 may adjust or otherwise modify values for one or more parameters utilized by the command generation application 510 when determining dosage commands, for example, by modifying a parameter value at a register or location in memory 506 referenced by the command generation application 510. In yet other embodiments, the personalization application 508 may predict meals or other events or activities that are likely to be engaged in by the patient and output or otherwise provide an indication of the predicted patient behavior, which, in turn, may then be utilized to adjust the manner in which dosage commands are generated to regulate glucose in a manner that accounts for the patient's predicted behavior in a personalized manner.

Still referring to FIG. 5, depending on the embodiment, the pump control module 502 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 502, or in any practical combination thereof. In exemplary embodiments, the pump control module 502 includes or otherwise accesses the data storage element or memory 506, which may be realized using any sort of non-transitory computer-readable medium capable of storing programming instructions for execution by the pump control module 502. The computer-executable programming instructions, when read and executed by the pump control module 502, cause the pump control module 502 to implement or otherwise generate the applications 508, 510 and perform tasks, operations, functions, and processes described herein.

It should be understood that FIG. 5 is a simplified representation of a pump control system 500 for purposes of explanation and is not intended to limit the subject matter described herein in any way. For example, in some embodiments, the features and/or functionality of the motor control module 412 may be implemented by or otherwise integrated into the pump control system 500 and/or the pump control module 502, for example, by the command generation application 510 converting the dosage command into a corresponding motor command, in which case, the separate motor control module 412 may be absent from an embodiment of the infusion device 402.

Figure 6:
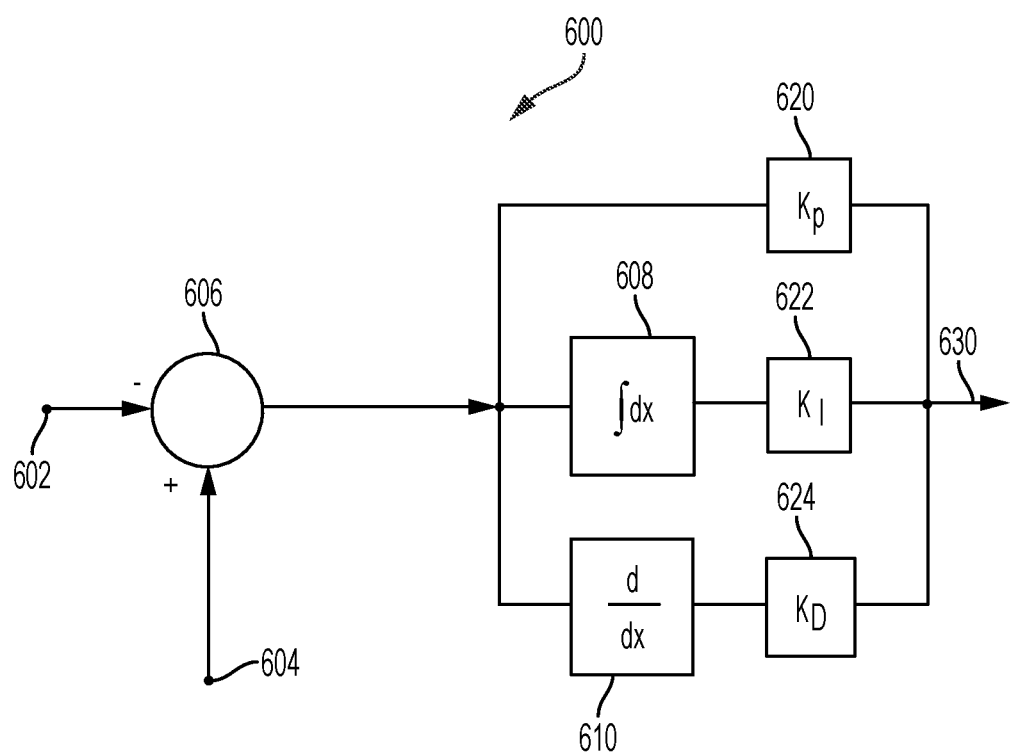
FIG. 6 is a block diagram of a closed-loop control system that may be implemented or otherwise supported by the pump control system in the fluid infusion device of FIGS. 4-5 in one or more exemplary embodiments.

FIG. 6 depicts an exemplary closed-loop control system 600 that may be implemented by a pump control system 420, 500 to provide a closed-loop operating mode that autonomously regulates a condition in the body of a patient to a reference (or target) value. It should be appreciated that FIG. 6 is a simplified representation of the control system 600 for purposes of explanation and is not intended to limit the subject matter described herein in any way.

In exemplary embodiments, the control system 600 receives or otherwise obtains a target glucose value at input 602. In some embodiments, the target glucose value may be stored or otherwise maintained by the infusion device 402 (e.g., in memory 506), however, in some alternative embodiments, the target value may be received from an external component (e.g., CCD 106 and/or computer 108). In one or more embodiments, the target glucose value may be calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 600 also receives or otherwise obtains a current glucose measurement value (e.g., the most recently obtained sensor glucose value) from the sensing arrangement 404 at input 604. The illustrated control system 600 implements or otherwise provides proportional-integral-derivative (PID) control to determine or otherwise generate delivery commands for operating the motor 432 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 602 and the measured glucose level at input 604 to generate or otherwise determine a dosage (or delivery) command provided at output 630. Based on that delivery command, the motor control module 412 operates the motor 432 to deliver insulin to the body of the patient to influence the patient's glucose level, and thereby reduce the difference between a subsequently measured glucose level and the target glucose level.

The illustrated control system 600 includes or otherwise implements a summation block 606 configured to determine a difference between the target value obtained at input 602 and the measured value obtained from the sensing arrangement 404 at input 604, for example, by subtracting the target value from the measured value. The output of the summation block 606 represents the difference between the measured and target values, which is then provided to each of a proportional term path, an integral term path, and a derivative term path. The proportional term path includes a gain block 620 that multiplies the difference by a proportional gain coefficient, KP, to obtain the proportional term. The integral term path includes an integration block 608 that integrates the difference and a gain block 622 that multiplies the integrated difference by an integral gain coefficient, KI, to obtain the integral term. The derivative term path includes a derivative block 610 that determines the derivative of the difference and a gain block 624 that multiplies the derivative of the difference by a derivative gain coefficient, KD, to obtain the derivative term. The proportional term, the integral term, and the derivative term are then added or otherwise combined to obtain a delivery command that is utilized to operate the motor at output 630. Various implementation details pertaining to closed-loop PID control and determining gain coefficients are described in greater detail in U.S. Pat. No. 7,402,153, which is incorporated by reference.

In one or more exemplary embodiments, the PID gain coefficients are patient-specific and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 402. The PID gain coefficients may be maintained by the memory 506 accessible to the pump control module 502. In this regard, the memory 506 may include a plurality of registers associated with the control parameters for the PID control. For example, a first parameter register may store the target glucose value and be accessed by or otherwise coupled to the summation block 606 at input 602, and similarly, a second parameter register accessed by the proportional gain block 620 may store the proportional gain coefficient, a third parameter register accessed by the integration gain block 622 may store the integration gain coefficient, and a fourth parameter register accessed by the derivative gain block 624 may store the derivative gain coefficient.

In one or more exemplary embodiments, one or more parameters of the closed-loop control system 600 are automatically adjusted or adapted in a personalized manner to account for potential changes in the patient's glucose level or insulin sensitivity resulting from meals, exercise, or other events or activities. For example, in one or more embodiments, the target glucose value 602 may be decreased in advance of a predicted meal event to achieve an increase in the insulin infusion rate to effectively pre-bolus a meal, and thereby reduce the likelihood of postprandial hyperglycemia. Additionally, or alternatively, the time constant or gain coefficient associated with one or more paths of the closed-loop control system 600 may be adjusted to tune the responsiveness to deviations between the measured glucose value 604 and the target glucose value 602. For example, based on the particular type of meal being consumed or the particular time of day during which the meal is consumed, the time constant associated with the derivative block 610 or derivative term path may be adjusted to make the closed-loop control more or less aggressive in response to an increase in the patient's glucose level based on the patient's historical glycemic response to the particular type of meal. As described in greater detail below in the context of FIGS. 21-22, in some embodiments, personalized adjustments are automatically performed proactively based on captured image content indicative of meals, exercise, or other events or activities likely to influence the patient's glucose level or insulin sensitivity.

Figure 7:
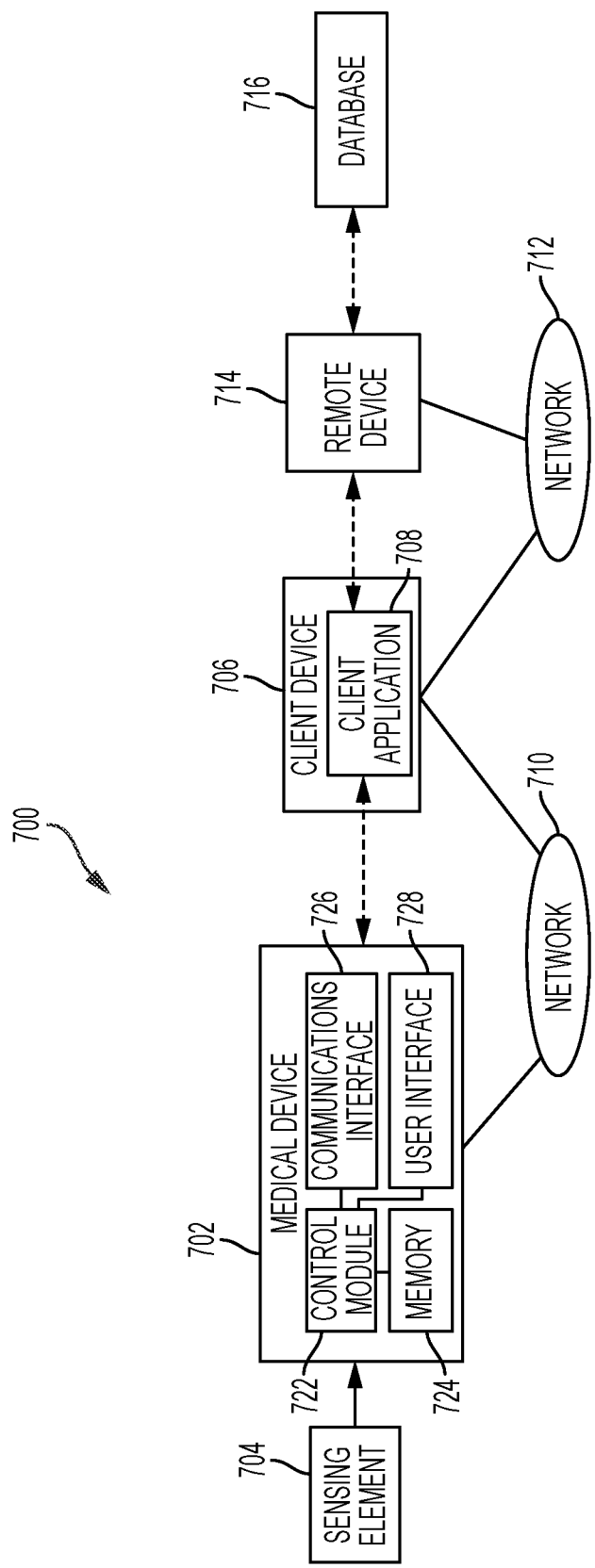
FIG. 7 is a block diagram of an exemplary patient monitoring system.

FIG. 7 depicts an exemplary embodiment of a patient monitoring system 700. The patient monitoring system 700 includes a medical device 702 that is communicatively coupled to a sensing element 704 that is inserted into the body of a patient or otherwise worn by the patient to obtain measurement data indicative of a physiological condition in the body of the patient, such as a sensed glucose level. The medical device 702 is communicatively coupled to a client device 706 via a communications network 710, with the client device 706 being communicatively coupled to a remote device 714 via another communications network 712. In this regard, the client device 706 may function as an intermediary for uploading or otherwise providing measurement data from the medical device 702 to the remote device 714. It should be appreciated that FIG. 7 depicts a simplified representation of a patient monitoring system 700 for purposes of explanation and is not intended to limit the subject matter described herein in any way.

In exemplary embodiments, the client device 706 is realized as a mobile phone, a smartphone, a tablet computer, or other similar mobile electronic device; however, in other embodiments, the client device 706 may be realized as any sort of electronic device capable of communicating with the medical device 702 via network 710, such as a laptop or notebook computer, a desktop computer, or the like. In exemplary embodiments, the network 710 is realized as a Bluetooth network, a ZigBee network, or another suitable personal area network. That said, in other embodiments, the network 710 could be realized as a wireless ad hoc network, a wireless local area network (WLAN), or local area network (LAN). The client device 706 includes or is coupled to a display device, such as a monitor, screen, or another conventional electronic display, capable of graphically presenting data and/or information pertaining to the physiological condition of the patient. The client device 706 also includes or is otherwise associated with a user input device, such as a keyboard, a mouse, a touchscreen, or the like, capable of receiving input data and/or other information from the user of the client device 706.

In some embodiments, a user, such as the patient, the patient's doctor or another healthcare provider, or the like, manipulates the client device 706 to execute a client application 708 that supports communicating with the medical device 702 via the network 710. In this regard, the client application 708 supports establishing a communications session with the medical device 702 on the network 710 and receiving data and/or information from the medical device 702 via the communications session. The medical device 702 may similarly execute or otherwise implement a corresponding application or process that supports establishing the communications session with the client application 708. The client application 708 generally represents a software module or another feature that is generated or otherwise implemented by the client device 706 to support the processes described herein. Accordingly, the client device 706 generally includes a processing system and a data storage element (or memory) capable of storing programming instructions for execution by the processing system, that, when read and executed, cause processing system to create, generate, or otherwise facilitate the client application 708 and perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof.

In one or more embodiments, the client device 706 and the medical device 702 establish an association (or pairing) with one another over the network 710 to support subsequently establishing a point-to-point or peer-to-peer communications session between the medical device 702 and the client device 706 via the network 710. For example, in accordance with one embodiment, the network 710 is realized as a Bluetooth network, wherein the medical device 702 and the client device 706 are paired with one another (e.g., by obtaining and storing network identification information for one another) by performing a discovery procedure or another suitable pairing procedure. The pairing information obtained during the discovery procedure allows either of the medical device 702 or the client device 706 to initiate the establishment of a secure communications session via the network 710.

In one or more exemplary embodiments, the client application 708 is also configured to store or otherwise maintain an address and/or other identification information for the remote device 714 on the second network 712. In this regard, the second network 712 may be physically and/or logically distinct from the network 710, such as, for example, the Internet, a cellular network, a wide area network (WAN), or the like. The remote device 714 generally represents a server or other computing device configured to receive and analyze or otherwise monitor measurement data, event log data, and potentially other information obtained for the patient associated with the medical device 702. In exemplary embodiments, the remote device 714 is coupled to a database 716 configured to store or otherwise maintain data associated with individual patients. In practice, the remote device 714 may reside at a location that is physically distinct and/or separate from the medical device 702 and the client device 706, such as, for example, at a facility that is owned and/or operated by or otherwise affiliated with a manufacturer of the medical device 702. For purposes of explanation, but without limitation, the remote device 714 may alternatively be referred to herein as a server.

Still referring to FIG. 7, the sensing element 704 generally represents the component of the patient monitoring system 700 that is configured to generate, produce, or otherwise output one or more electrical signals indicative of a physiological condition that is sensed, measured, or otherwise quantified by the sensing element 704. In this regard, the physiological condition of a patient influences a characteristic of the electrical signal output by the sensing element 704, such that the characteristic of the output signal corresponds to or is otherwise correlative to the physiological condition that the sensing element 704 is sensitive to. In exemplary embodiments, the sensing element 704 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 704.

The medical device 702 generally represents the component of the patient monitoring system 700 that is communicatively coupled to the output of the sensing element 704 to receive or otherwise obtain the measurement data samples from the sensing element 704 (e.g., the measured glucose and characteristic impedance values), store or otherwise maintain the measurement data samples, and upload or otherwise transmit the measurement data to the server 714 via the client device 706. In one or more embodiments, the medical device 702 is realized as an infusion device 102, 200, 402 configured to deliver a fluid, such as insulin, to the body of the patient. That said, in other embodiments, the medical device 702 could be a standalone sensing or monitoring device separate and independent from an infusion device (e.g., sensing arrangement 104, 404), such as, for example, a continuous glucose monitor (CGM), an interstitial glucose sensing arrangement, or similar device. It should be noted that although FIG. 7 depicts the medical device 702 and the sensing element 704 as separate components, in practice, the medical device 702 and the sensing element 704 may be integrated or otherwise combined to provide a unitary device that can be worn by the patient.

In exemplary embodiments, the medical device 702 includes a control module 722, a data storage element 724 (or memory), a communications interface 726, and a user interface 728. The user interface 728 generally represents the input user interface element(s) and/or output user interface element(s) associated with the medical device 702 (e.g., one or more of user interface elements 226, 230, 440). The control module 722 generally represents the hardware, circuitry, logic, firmware and/or other component(s) of the medical device 702 that is coupled to the sensing element 704 to receive the electrical signals output by the sensing element 704 and perform or otherwise support various additional tasks, operations, functions and/or processes described herein. Depending on the embodiment, the control module 722 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the control module 722 includes an analog-to-digital converter (ADC) or another similar sampling arrangement that samples or otherwise converts an output electrical signal received from the sensing element 704 into corresponding digital measurement data value. In other embodiments, the sensing element 704 may incorporate an ADC and output a digital measurement value.

The communications interface 726 generally represents the hardware, circuitry, logic, firmware and/or other components of the medical device 702 that are coupled to the control module 722 for outputting data and/or information from/to the medical device 702 to/from the client device 706. For example, the communications interface 726 may include or otherwise be coupled to one or more transceiver modules capable of supporting wireless communications between the medical device 702 and the client device 706. In exemplary embodiments, the communications interface 726 is realized as a Bluetooth transceiver or adapter configured to support Bluetooth Low Energy (BLE) communications.

In exemplary embodiments, the remote device 714 receives, from the client device 706, measurement data values associated with a particular patient (e.g., sensor glucose measurements, acceleration measurements, and the like) that were obtained using the sensing element 704, and the remote device 714 stores or otherwise maintains the historical measurement data in the database 716 in association with the patient (e.g., using one or more unique patient identifiers). Additionally, the remote device 714 may also receive, from or via the client device 706, meal data or other event log data that may be input or otherwise provided by the patient (e.g., via client application 708) and store or otherwise maintain historical meal data and other historical event or activity data associated with the patient in the database 716. In this regard, the meal data include, for example, a time or timestamp associated with a particular meal event, a meal type or other information indicative of the content or nutritional characteristics of the meal, and an indication of the size associated with the meal. In exemplary embodiments, the remote device 714 also receives historical fluid delivery data corresponding to basal or bolus dosages of fluid delivered to the patient by an infusion device 102, 200, 402. For example, the client application 708 may communicate with an infusion device 102, 200, 402 to obtain insulin delivery dosage amounts and corresponding timestamps from the infusion device 102, 200, 402, and then upload the insulin delivery data to the remote device 714 for storage in association with the particular patient. The remote device 714 may also receive geolocation data and potentially other contextual data associated with a device 702, 706 from the client device 706 and/or client application 708, and store or otherwise maintain the historical operational context data in association with the particular patient. In this regard, one or more of the devices 702, 706 may include a global positioning system (GPS) receiver or similar modules, components or circuitry capable of outputting or otherwise providing data characterizing the geographic location of the respective device 702, 706 in real-time.

The historical patient data may be analyzed by one or more of the remote device 714, the client device 706, and/or the medical device 702 to alter or adjust operation of an infusion device 102, 200, 402 to influence fluid delivery in a personalized manner. For example, the patient's historical meal data and corresponding measurement data or other contextual data may be analyzed to predict a future time when the next meal is likely to be consumed by the patient, the likelihood of a future meal event within a specific time period, the likely size or amount of carbohydrates associated with a future meal, the likely type or nutritional content of the future meal, and/or the like. Moreover, the patient's historical measurement data for postprandial periods following historical meal events may be analyzed to model or otherwise characterize the patient's glycemic response to the predicted size and type of meal for the current context (e.g., time of day, day of week, geolocation, etc.). One or more aspects of the infusion device 102, 200, 402 that control or regulate insulin delivery may then be modified or adjusted to proactively account for the patient's likely meal activity and glycemic response.

In one or more exemplary embodiments, the remote device 714 utilizes machine learning to determine which combination of historical sensor glucose measurement data, historical delivery data, historical auxiliary measurement data (e.g., historical acceleration measurement data, historical heart rate measurement data, and/or the like), historical event log data, historical geolocation data, and other historical or contextual data are correlated to or predictive of the occurrence of a particular event, activity, or metric for a particular patient, and then determines a corresponding equation, function, or model for calculating the value of the parameter of interest based on that set of input variables. Thus, the model is capable of characterizing or mapping a particular combination of one or more of the current (or recent) sensor glucose measurement data, auxiliary measurement data, delivery data, geographic location, patient behavior or activities, and the like to a value representative of the current probability or likelihood of a particular event or activity or a current value for a parameter of interest. It should be noted that since each patient's physiological response may vary from the rest of the population, the subset of input variables that are predictive of or correlative for a particular patient may vary from other patients. Additionally, the relative weightings applied to the respective variables of that predictive subset may also vary from other patients who may have common predictive subsets, based on differing correlations between a particular input variable and the historical data for that particular patient. It should be noted that any number of different machine learning techniques may be utilized by the remote device 714 to determine what input variables are predictive for a current patient of interest, such as, for example, artificial neural networks, genetic programming, support vector machines, Bayesian networks, probabilistic machine learning models, or other Bayesian techniques, fuzzy logic, heuristically derived combinations, or the like.

Medical Device Assistance Using Augmented Reality

Referring now to FIGS. 8-17, in one or more exemplary embodiments, augmented reality is utilized to provide guidance information that assists a patient or other user in configuring or otherwise managing a medical device, such as an infusion device 102, 200, 402, 702 or a sensing device 104, 404, 406, 704. For example, augmented reality may be utilized to interactively provide overlaid guidance information to help facilitate the patient adjusting or otherwise configuring patient-specific settings or performing other personalization that influences the manner in which an infusion device 102, 200, 402, 702 autonomously operates to deliver fluid to the patient.

Figure 8:
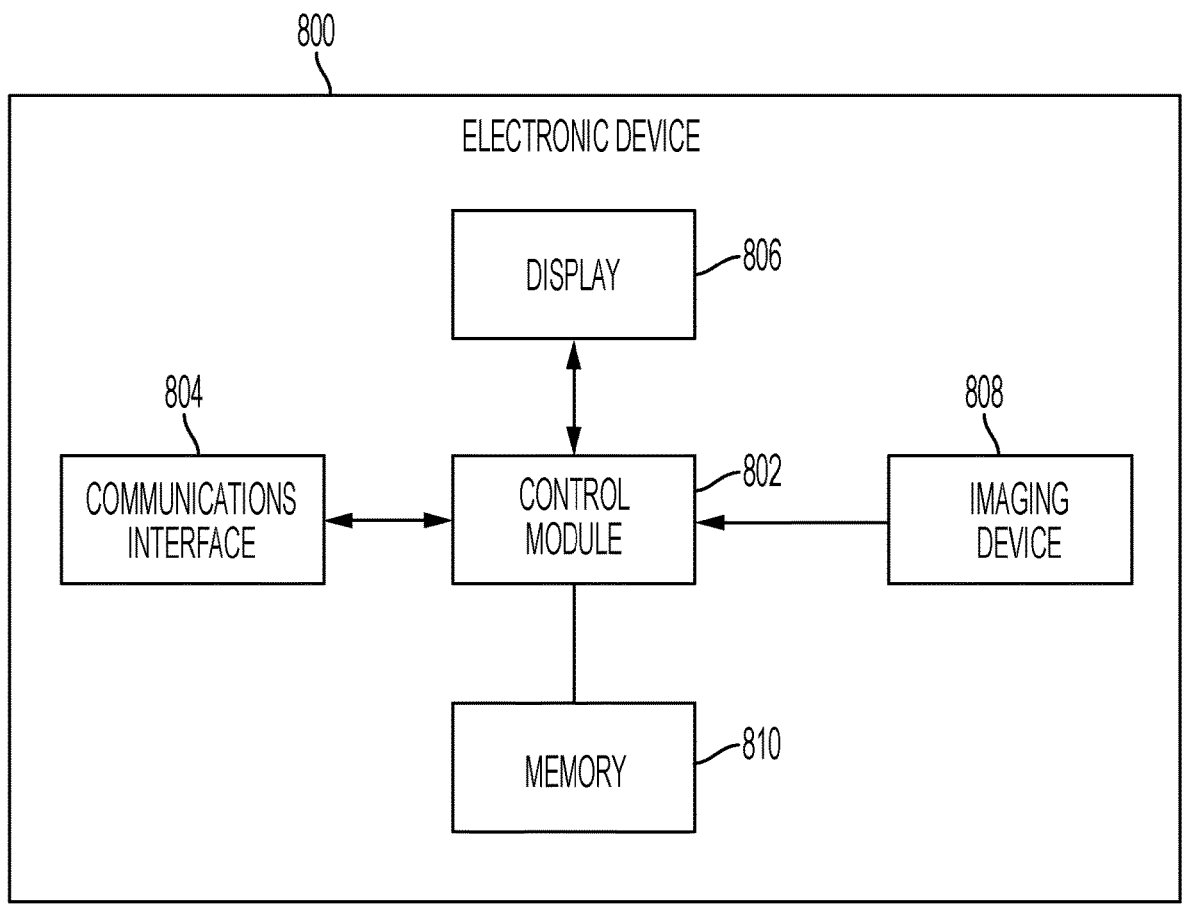
FIG. 8 is a block diagram of an exemplary electronic device suitable for use in connection with a medical device in one or more exemplary embodiments.

FIG. 8 depicts an exemplary embodiment of an electronic device 800 suitable for use in connection with a medical device in conjunction with the augmented-reality related processes described herein. Depending on the embodiment, the electronic device 800 could be realized as a client computing device 106, 706, such as a mobile phone or the like, or alternatively, the electronic device 800 could be realized as an auxiliary device, such as a headset, smartglasses, or the like that may be capable of communicating with various other devices or components in an infusion system 100, 400 or patient management system 700, as described herein. The illustrated electronic device 800 includes, without limitation, a control module 802, a communications interface 804, a display device 806, an imaging device 808, and a data storage element (or memory) 810. The control module 802 is coupled to the communications interface 804, the memory 810, the display device 806, and the imaging device 808, and the control module 802 is suitably configured to support the operations, tasks, and/or processes described herein. It should be understood that FIG. 8 is a simplified representation of an electronic device 800 for purposes of explanation and is not intended to limit the subject matter described herein in any way.

The communications interface 804 generally represents the hardware, circuitry, logic, firmware and/or other components of the electronic device 800 that are coupled to the control module 802 and configured to support communications sessions between the auxiliary device 800 and one or more other devices via a network (e.g., network 110). In this regard, the communications interface 804 may include or otherwise be coupled to one or more transceiver modules capable of supporting wireless communications. In other embodiments, the communications interface 804 may be configured to support wired communications to/from the auxiliary device.

The display device 806 may be realized as any sort of display element capable of graphically displaying or otherwise depicting information or other data under control of the control module 802. In this regard, in some embodiments, the display device 806 may be transparent or otherwise include a transparent element (e.g., a lens) utilized in concert with a projector to provide heads-up display (HUD) functionality or otherwise support projecting or reflecting overlays in a manner that allows a user to see through or behind the display device 806. In exemplary embodiments, the imaging device 808 is realized as a camera; however, it should be noted that the subject matter described herein is not limited to cameras or any particular type of camera, and in various embodiments, the imaging device 808 may be realized using any number, type, or configuration of image sensors or other suitable devices capable of capturing imagery of the surrounding environment. That said, for ease of explanation, but without limitation, the imaging device 808 may alternatively be referred to herein as a camera.

The control module 802 generally represents the hardware, circuitry, logic, firmware and/or other component of the electronic device 800 configured to support augmented reality and perform various additional tasks, operations, functions and/or operations described herein. Depending on the embodiment, the control module 802 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the control module 802, or in any practical combination thereof. In exemplary embodiments, the control module 802 includes or otherwise accesses the data storage element or memory 810, which may be realized using any sort of non-transitory computer-readable medium capable of storing programming instructions for execution by the control module 802. The computer-executable programming instructions, when read and executed by the control module 802, cause the control module 802 to implement or otherwise generate one or more software applications and perform tasks, operations, functions, and processes described herein.

In one or more exemplary embodiments, the memory 810 stores or otherwise maintains a user guide or other troubleshooting information for a medical device including, but not limited to, reference GUI displays that may be presented on the medical device, sequences or logical relationships between GUI displays, relationships between GUI displays and medical device settings, information pertaining to the various modes or features of the medical device, variables, parameters, or other values that are capable of being programmed, configured, entered, or otherwise established for use by a particular mode or feature of the medical device, including user-configurable variables, parameters, or other values that may be programmed, configured, entered or otherwise established for a patient-specific implementation of a particular mode or feature of the medical device. That said, in other embodiments, the user guide or other troubleshooting information may be stored remotely (e.g., in database 716) and retrieved by the electronic device 800 (e.g., via network 712) and temporarily stored in the memory 810 on an as-needed basis. Additionally, in connection with the subject matter described herein, the memory 810 may be utilized to store captured images or sequences thereof, or alternatively, images captured by the by the imaging device 816 may be transferred, uploaded, or otherwise transmitted to a remote device (e.g., remote device 714) to be analyzed and/or stored remotely (e.g., in database 716).

In some embodiments described herein, the memory 810 may also store or otherwise maintain settings information for a medical device including, but not limited to, data indicating which modes or features of the medical device have been configured, data indicating which modes or features of the medical device have not been configured, data indicating which modes or features of the medical device are enabled or activated, data indicating which modes or features of the medical device have been disabled or deactivated, variables, parameters, or other values that have been programmed, configured, entered, or otherwise established for use by a particular mode or feature of the medical device, and any patient-specific variables, parameters, or other values that have been programmed, configured, entered or otherwise established for use by a particular mode or feature of the medical device. In this regard, the settings information may include configuration data for an operating mode of the medical device, configuration data for a feature of the medical device, or values or data for other patient-specific settings, parameters, or variables. For example, for an infusion device, the settings information could include a value for a basal rate, a patient-specific insulin sensitivity factor, a patient-specific insulin-to-carbohydrate ratio, a patient-specific total daily insulin requirement, or the like. That said, in other embodiments, the settings information may be stored elsewhere (e.g., at a medical device 702, 704 or remote device 714, 716) and retrieved by the electronic device 800 (e.g., via network 710 or other communications established between devices) and temporarily stored in the memory 810 on an as-needed basis.

Figure 9:
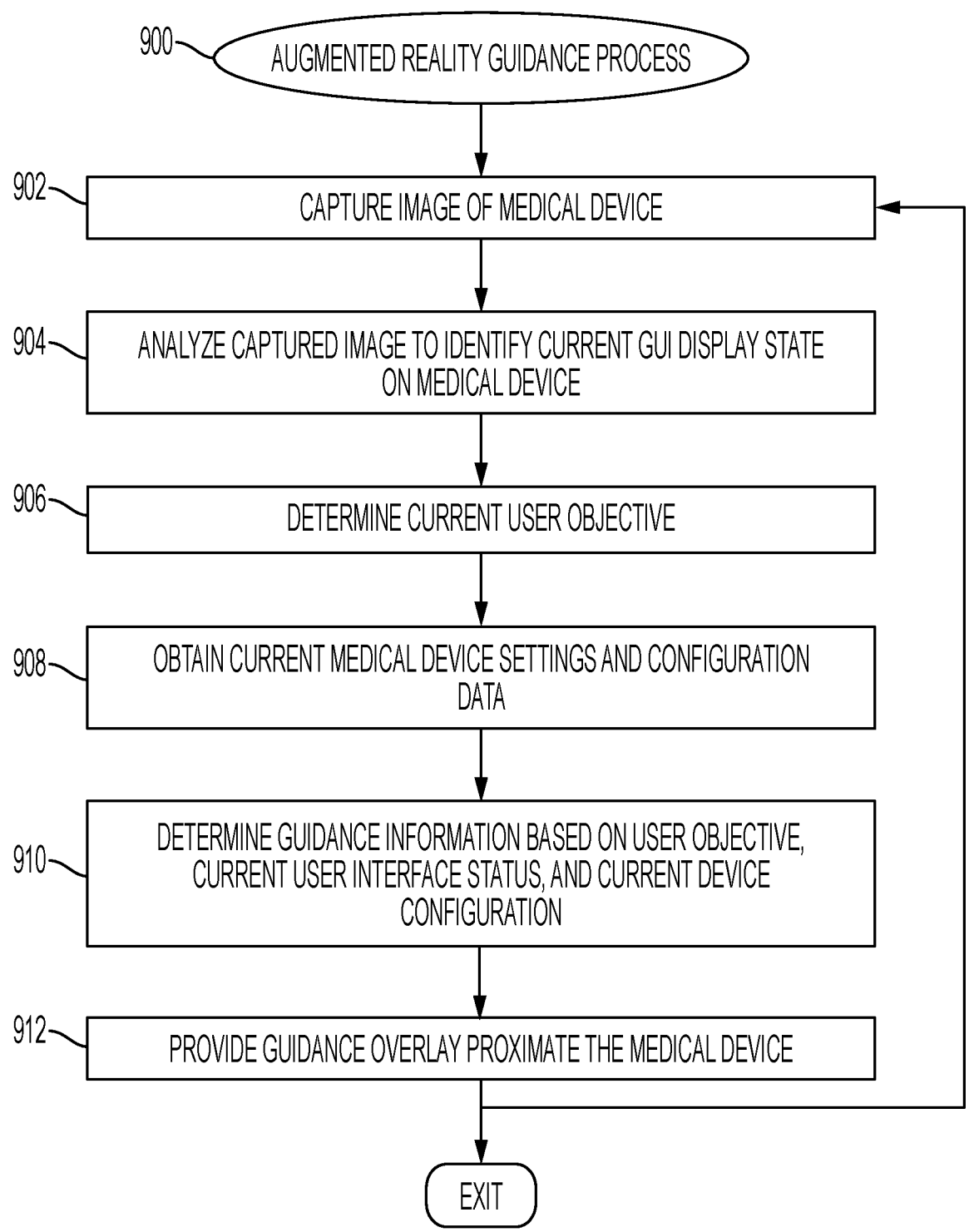
FIG. 9 is a flow diagram of an exemplary augmented reality guidance process suitable for use with a medical device in one or more exemplary embodiments.

FIG. 9 depicts an exemplary augmented reality guidance process 900 for providing guidance to a patient or user in real-time based on the current state of his or her medical device to facilitate achieving the desired operation of the medical device, such as infusion device 102, 200, 402, 702. As described in greater detail below, a captured image of the medical device is analyzed to determine the current state of the GUI presented at the medical device (e.g., on a display device 226, 440, 728). Guidance information pertaining to the current state of the GUI is determined and presented to the user using a guidance overlay that is depicted proximate the medical device using augmented reality, thereby allowing the user to concurrently view the guidance information and the GUI of the medical device while interacting with the medical device. Depending on the embodiment, the guidance information may be influenced by an identified objective of the user, the current settings information of the medical device and/or other contextual information in addition to the current state of the GUI.

The various tasks performed in connection with the augmented reality guidance process 900 may be performed by hardware, firmware, software executed by processing circuitry, or any combination thereof. For illustrative purposes, the following description refers to elements mentioned above in connection with FIGS. 1-8. For purposes of explanation, the augmented reality guidance process 900 may be described herein primarily in the context of being implemented at a client device 706, 800 in a patient management system 700. It should be appreciated that the augmented reality guidance process 900 may include any number of additional or alternative tasks, the tasks need not be performed in the illustrated order and/or the tasks may be performed concurrently, and/or the augmented reality guidance process 900 may be incorporated into a more comprehensive procedure or process having additional functionality not described in detail herein. Moreover, one or more of the tasks shown and described in the context of FIG. 9 could be omitted from a practical embodiment of the augmented reality guidance process 900 as long as the intended overall functionality remains intact.

In the illustrated embodiment, the augmented reality guidance process 900 begins by capturing or otherwise obtaining one or more images of the medical device and analyzing or otherwise processing the image to identify the current state of the user interface of the medical device (tasks 902, 904). In this regard, the patient may orient or otherwise position an electronic device 706, 800 such that its imaging device 808 captures imagery of at least a portion of the user interface of the medical device 702 (e.g., at least a portion of the display 226). The control module 802 receives or otherwise obtains the image(s) captured by the imaging device 808 and utilizes computer vision techniques to analyze or otherwise compare the captured image(s) to reference GUI displays or other user guide information maintained in the memory 810 or obtained from a remote device (e.g., database 716). For example, the control module 802 may receive images from the imaging device 808 on a substantially continuous basis and continually perform image recognition, optical character recognition, and/or the like to attempt to classify or otherwise identify the current GUI display depicted at the medical device 702 and the current state of that GUI display by mapping or otherwise matching a captured image of the GUI display to a reference GUI display. In this regard, based on the analysis of the image(s) from the imaging device 808, the control module 802 identifies or otherwise determines the current screen, menu, or other GUI display presented by the medical device 702, along with identifying the position or state of a user input selection (or a mouse, icon, or other graphical representation thereof) on the screen, menu, or other GUI display presented on the medical device 702.

The augmented reality guidance process 900 continues by identifying or otherwise determining the current objective of the user (task 906), that is, what the patient or user of the electronic device 706, 800 is trying to accomplish or achieve using the medical device 702 or what feature or aspect of the medical device 702 is of interest to the patient. In some embodiments, the control module 802 may inferentially determine the current user objective based on the current GUI display presented at the medical device 702 and/or the current state of the user input selection. For example, if the captured image of the GUI display at the medical device 702 includes an active alert or notification that is selected or highlighted by the user input selection, the control module 802 may determine the patient's objective is to resolve or understand the current alert or notification. It should be noted that are numerous different potential device statuses and corresponding objectives that may be determined based thereon, and the subject matter described herein is not limited to any particular example described herein. In yet other embodiments, the control module 802 may generate or otherwise provide a GUI display that allows the patient to select, input, or otherwise indicate what the patient's objective is. For example, the control module 802 may implement or otherwise execute a client application that generates or otherwise provides a list of selectable GUI elements, where each of the GUI elements corresponds to a different objective.

In one or more embodiments, the augmented reality guidance process 900 also identifies or otherwise obtains the current operational settings or configuration of the medical device (task 908). For example, as described above, the settings or configuration data stored or otherwise maintained onboard an infusion device 102, 200, 402, 702 pertaining to the various modes, features, or other patient-specific or patient-configurable operations supported by the infusion device 102, 200, 402, 702 may be obtained from the infusion device 102, 200, 402, 702 (e.g., via network 710) and/or maintained in the local memory 810. In this regard, the current device settings information may indicate the modes or features supported by the infusion device 102, 200, 402, 702 that have been enabled, activated, or configured, which modes or features supported by the infusion device 102, 200, 402, 702 that have been disabled or deactivated, which patient-specific control parameters, variables, or other patient settings for which values have been defined, entered or otherwise provided, and which patient-specific control parameters, variables, or other patient settings for which no values are maintained by the infusion device 102, 200, 402, 702.

Based on the user's objective, the current user interface status, and the current device settings, the augmented reality guidance process 900 determines guidance information pertaining to the user's objective given the current user interface status and the current device settings and then generates or otherwise provides an overlay proximate the medical device that includes the guidance information that indicates or otherwise explains how the user can achieve the objective (tasks 910, 912). For example, the control module 802 may utilize the user guide information associated with the medical device 702 to identify or otherwise determine one or more actions that the user can take with respect to the current GUI display to achieve the user's objective given the current medical device settings. In this regard, the guidance information is consistent with (or context-sensitive to) both the current operational settings and the current patient-specific settings maintained by the medical device 702, while also being context-sensitive to reflect the current GUI display on the medical device 702 and/or the current state of user interaction with respect to that GUI display on the medical device 702. That is, the guidance information is not incompatible or inconsistent with current settings maintained by the medical device 702, and the guidance information also is not incompatible or inconsistent with the current user interface status of the medical device 702. An overlay including the guidance information is then depicted proximate the medical device 702 using augmented reality, thereby allowing the patient or user to concurrently view the guidance information and the GUI display presented on the medical device 702. For example, the guidance overlay may be provided adjacent to a menu or list on the medical device 702 (e.g., at or near the top or bottom of the menu or list) or provided adjacent to the user input selection on the GUI display, thereby facilitating cross-referencing the guidance information with the GUI display at the medical device 702 without diverting his or her eyes.

The loop defined by tasks 902, 904, 906, 908, 910 and 912 may repeat indefinitely while imagery of the medical device is captured to dynamically update the guidance overlays in real-time as the user interacts with the medical device. In this regard, in response to a detecting a change in the GUI at the medical device 702 based on the captured image(s), the augmented reality guidance process 900 dynamically updates the guidance information to reflect the change in user interface state, for example, by providing updated instructions or actions that the user can take to achieve the objective from the current GUI display.

Figure 11:
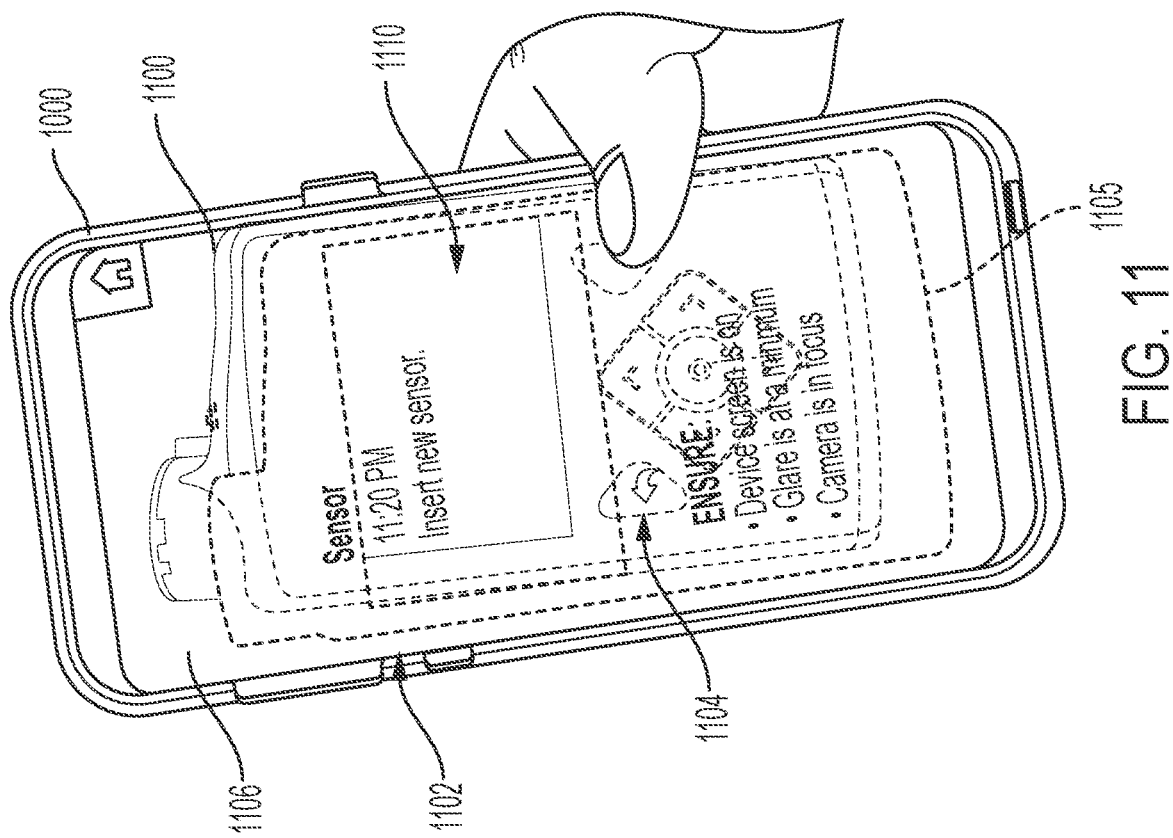
FIGS. 10-17 depict exemplary embodiments of augmented reality graphical user interface (GUI) displays suitable for presentation by an electronic device in connection with the augmented reality guidance process of FIG. 9.
Figure 10:
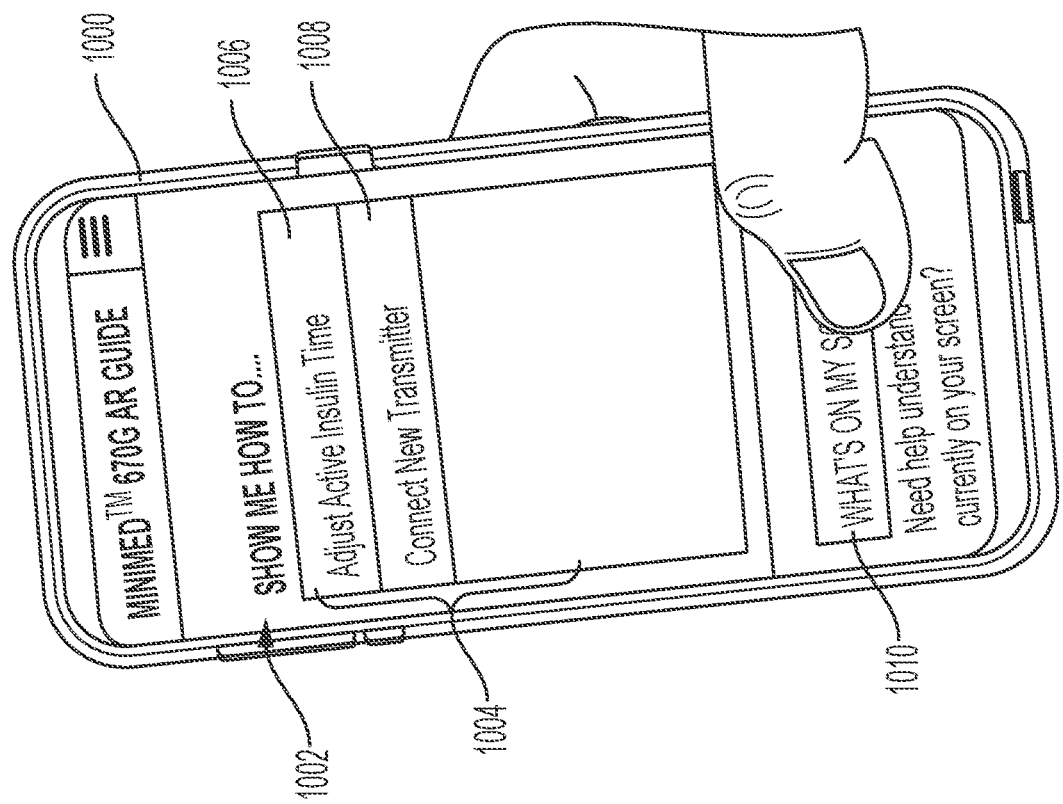
Figure 12:
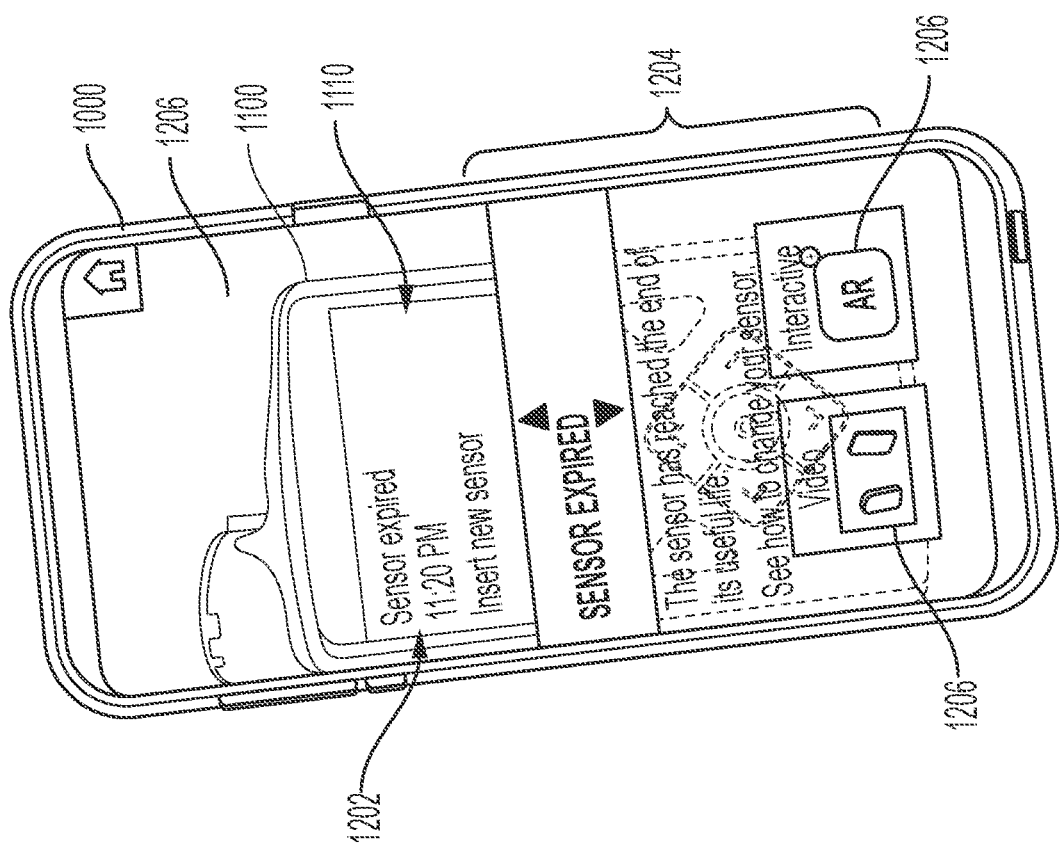

FIGS. 10-12 depict an exemplary sequence of displays that may be presented by or on an electronic device 1000 (e.g., client computing device 706 or electronic device 800) in connection with the augmented reality guidance process 900 of FIG. 9. In this regard, it should be noted that while FIGS. 10-12 depict an embodiment where the electronic device 1000 is realized as a mobile device (e.g., a smartphone) for obtaining guidance information pertaining to an infusion device 1100 (e.g., infusion device 102, 200, 402, 702), the subject matter described herein is not limited to mobile phones or infusion devices and may be implemented in an equivalent manner using other electronic devices (e.g., smartglasses or the like) or in the context of other medical devices (e.g., continuous glucose monitoring (CGM) devices or the like).

Referring to FIG. 10, in some embodiments, the augmented reality guidance process 900 may be initiated or triggered from an initial GUI display 1002 generated or otherwise provided by a client application (e.g., client application 706) executing on a patient's mobile device 1000 that enables the patient to input or otherwise provide indication of his or her objective with respect to the infusion device 1100. In this regard, the initial GUI display 1002 may include a menu or list 1004 of selectable GUI elements corresponding to potential objectives. For example, the illustrated embodiment depicts a first selectable GUI element 1006 corresponding to an objective of adjusting the patient's active insulin time, a second selectable GUI element 1008 corresponding to an objective of connecting the infusion device 1100 to a new sensing arrangement (e.g., sensing arrangement 104, 404, 704), and a third selectable GUI element 1010 corresponding to an objective of understanding the current GUI display presented on the infusion device 1100.

Referring to FIG. 11, in response to a user selection of the selectable GUI element 1010 for understanding the current GUI display presented on the infusion device 1100, the client application executing on the mobile device 1000 generates an augmented reality GUI display 1102 that includes a semi-transparent graphical overlay 1104 that overlies a graphical representation 1106 of the imagery captured by the imaging device (e.g., imaging device 808) of the mobile device 1000. In this regard, the graphical overlay 1104 includes a graphical representation of an infusion device outline 1105 that provides guidance for how the patient or user should position or orient the infusion device 1100 with respect to the mobile device 1000, or vice versa, to thereby capture images of the infusion device 1100 that include a sufficient portion of the GUI display 1110 at the infusion device 1100 for analysis in connection with the augmented reality guidance process 900.

Referring to FIG. 12, in response to the imaging device capturing a sufficient portion of the infusion device GUI display 1110, the client application utilizes image recognition or other image processing techniques to map or otherwise correlate the current GUI display 1110 to a particular reference GUI display, which, in turn is then utilized to obtain additional user guide information relevant to the current GUI display for formulating guidance information. For example, in the illustrated embodiment, the current infusion device GUI display 1110 is recognized (e.g., task 904) as a GUI display for an expired sensing element (e.g., sensing element 704), and based on the user objective of understanding the current GUI display, the client application retrieves or otherwise obtains the user guide information associated with the expired sensing element GUI display and then generates corresponding guidance information that explains the expired sensing element GUI display (e.g., task 910). Thereafter, the client application generates an updated augmented reality GUI display 1202 on the mobile device 1000 that includes a graphical representation of the generated guidance information 1204 visually overlying the graphical representation 1106 of the imagery captured by the phone's imaging device, resulting in the guidance information overlay being depicted proximate the infusion device 1100 in a manner that allows the patient to concurrently view the infusion device GUI display 1110 and the corresponding guidance information 1204. In the illustrated embodiment, the guidance information 1204 informs the patient of the need to replace or change the sensing element and includes selectable GUI elements 1206 that may be selected by the patient to initiate presentation of additional guidance GUI displays on the mobile device 1000 related to the current infusion device GUI display 1110.

Figure 13:
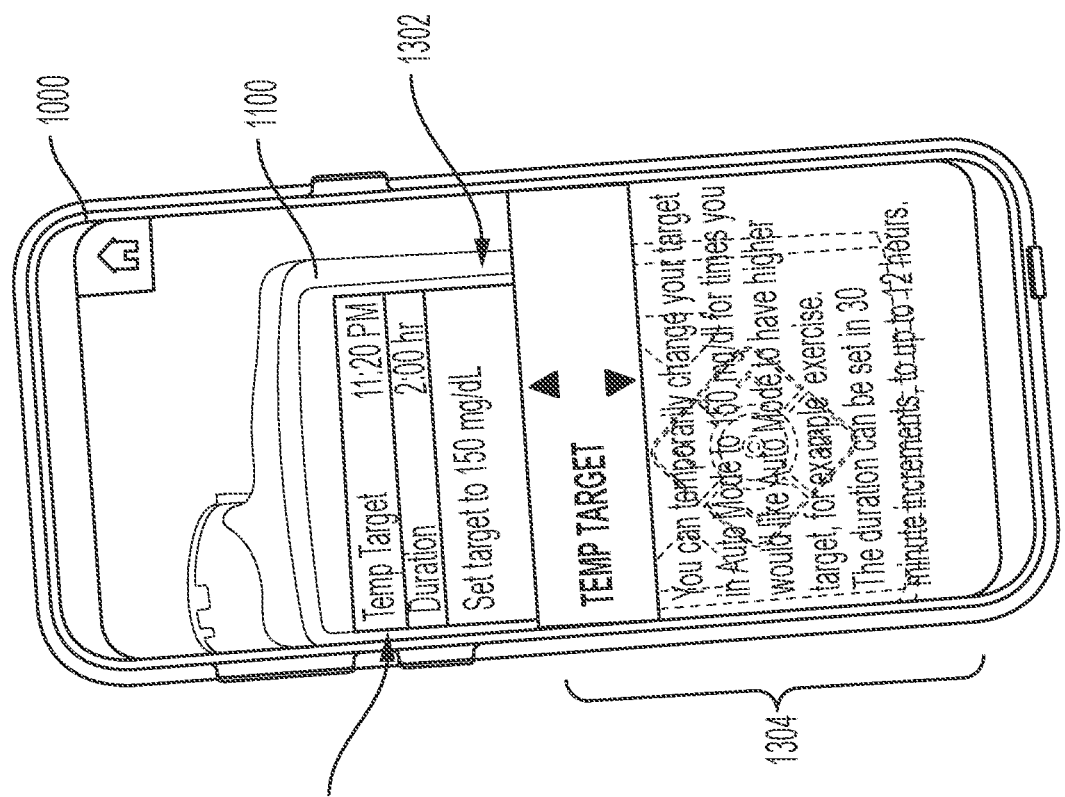

FIG. 13 depicts another example where the patient is attempting to understand an infusion device GUI display 1310 pertaining to control parameters for an autonomous operating mode supported by the infusion device 1100 (e.g., a closed-loop operating mode, an open-loop operating mode, or the like). For example, in the illustrated embodiment, the current infusion device GUI display 1310 is recognized as a GUI display for setting a temporary target glucose value for an autonomous operating mode, and the client application generates corresponding guidance information that explains what the target glucose value represents and how the patient can set the temporary target glucose value and/or set the duration for which the temporary target glucose value is utilized in a patient-specific manner. In some embodiments, the client application may also retrieve or otherwise obtain the current temporary target glucose value, the current temporary target duration and/or other current infusion device settings and provide guidance information that reflects or is otherwise influenced by the current infusion device settings. For example, current infusion device settings that are not presented on the temporary target GUI display 1310 may be indicated by or included with the explanatory guidance information, thereby facilitating a greater understanding on behalf of the patient of how adjusting the temporary target settings could interact with the current device settings. As another example, if the infusion device GUI display pertains to an autonomous operating mode that is not currently enabled based on the current device configuration evidenced by the device settings, the guidance information may explain how the patient could enable that mode and/or why the patient may or may not want to enable the mode, or vice versa. Thereafter, the client application generates an augmented reality GUI display 1302 on the mobile device 1000 that includes a graphical representation of the generated guidance information 1304 visually overlying the graphical representation the infusion device 1100 in a manner that allows the patient to concurrently view the temporary target GUI display 1310 on the infusion device 1100 and the corresponding guidance information 1304.

Figure 15:
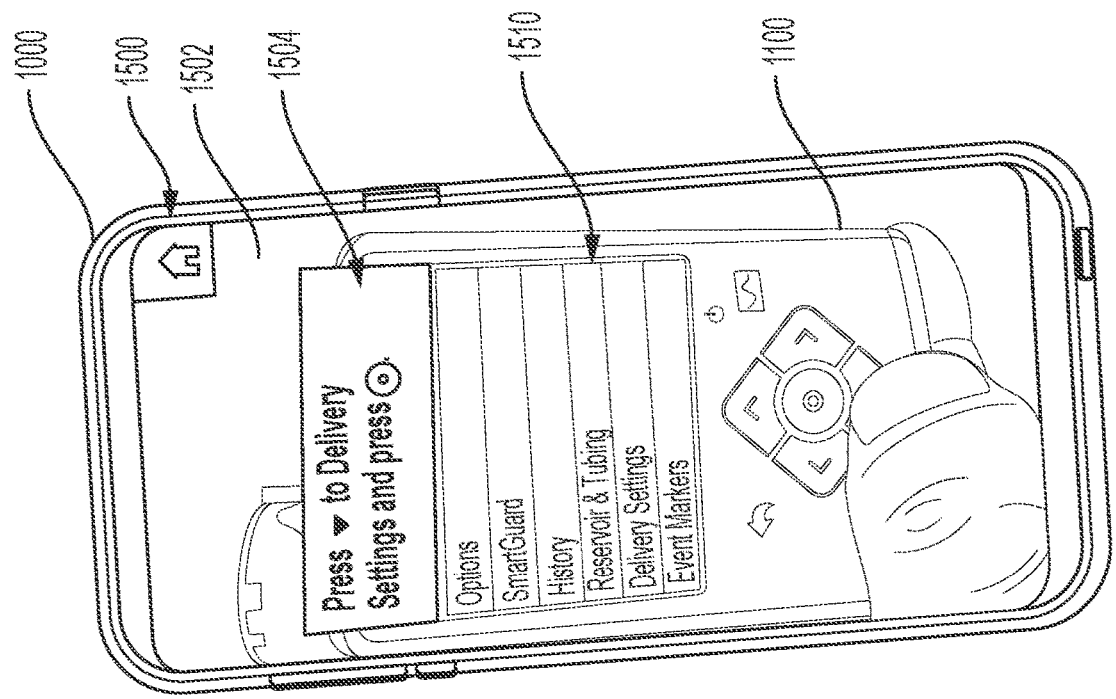
Figure 14:
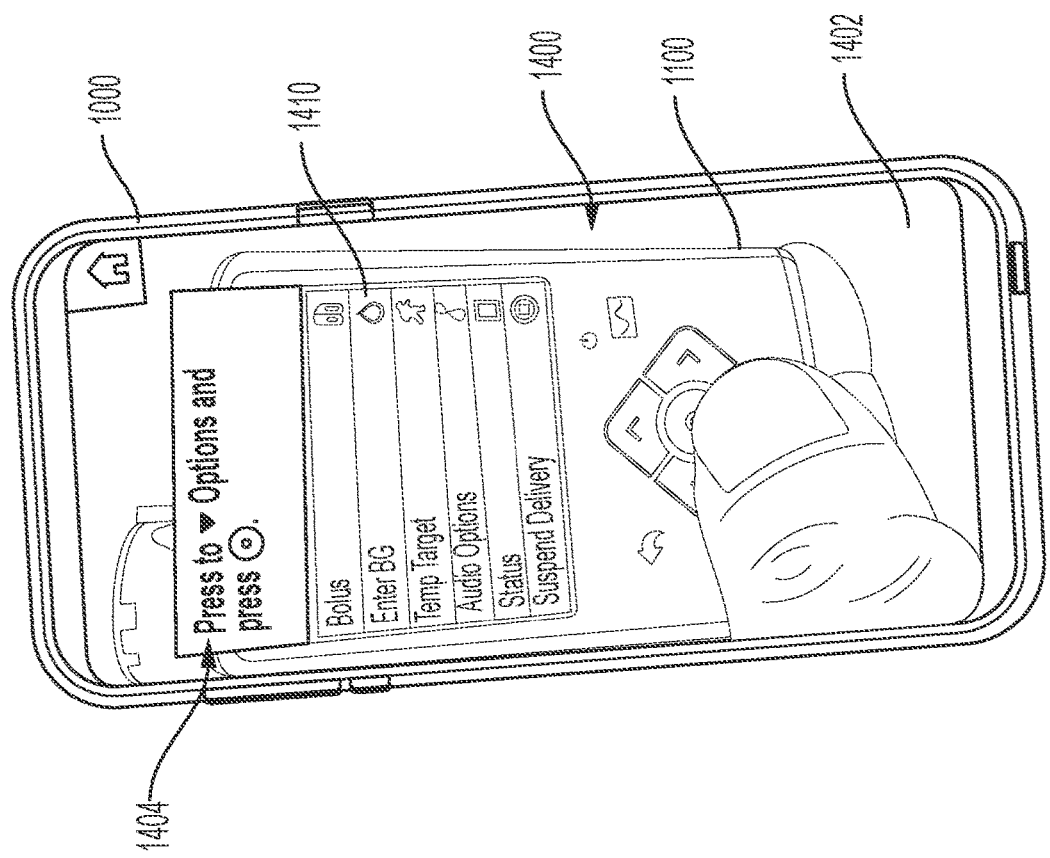
Figure 16:
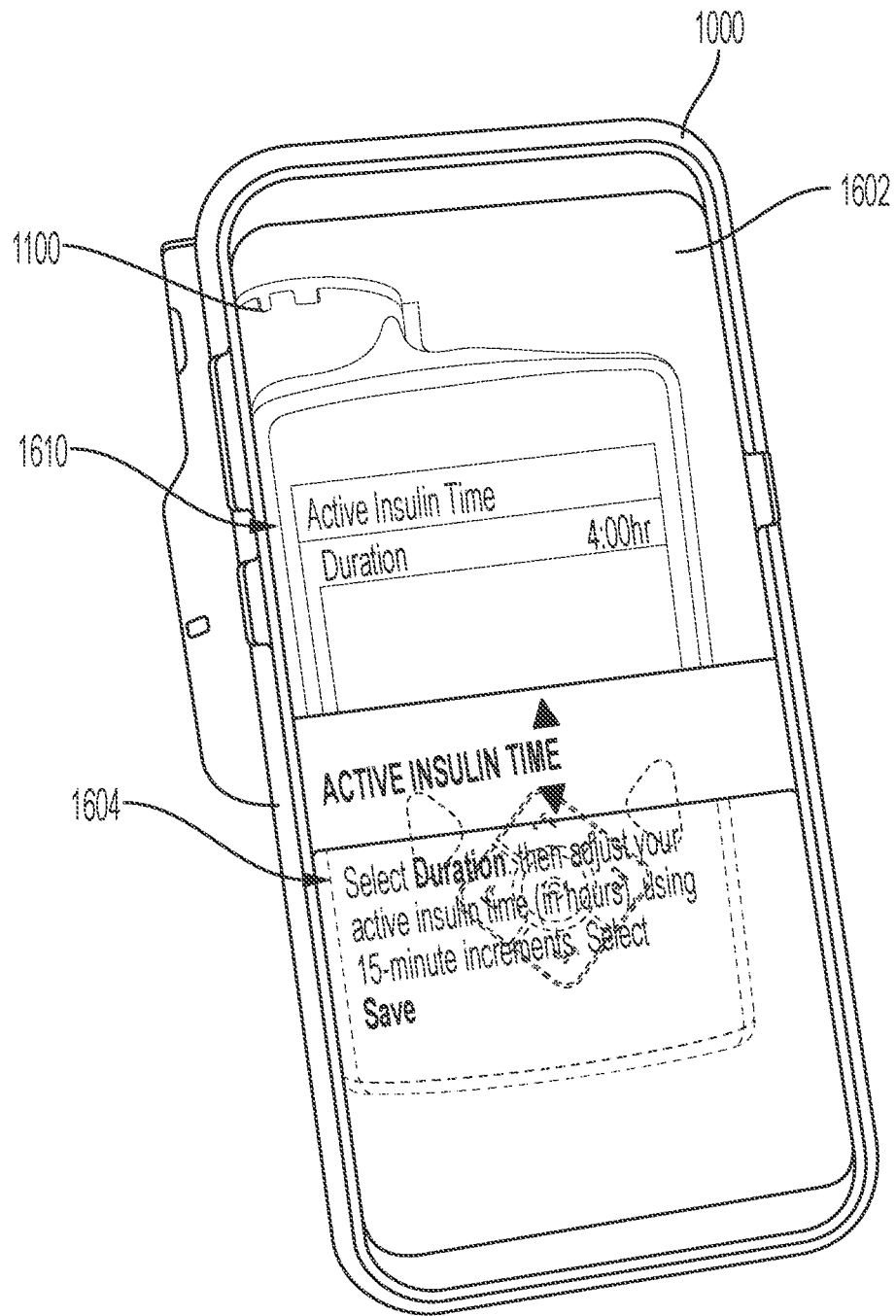

FIGS. 14-16 depict an exemplary sequence of augmented reality GUI displays that may be presented on the patient's mobile device 1000 in connection with the augmented reality guidance process 900 of FIG. 9 in response to selection of the GUI element 1006 indicating a user objective to set an active insulin time. Thereafter, the client application on the mobile device 1000 generates an augmented reality GUI display 1400 that includes a graphical representation 1402 of the imagery captured by the imaging device of the mobile device 1000. In response to the imaging device capturing a sufficient portion of the infusion device GUI display 1410, the client application utilizes image recognition or other image processing techniques to map or otherwise correlate the current GUI display 1410 to the main menu GUI display, and then utilizes the user guide information for the infusion device 1100 to determine what sequence of actions a user needs to take in order to arrive at a GUI display from the main menu GUI display that will ultimately allow the active insulin time to be set or adjusted by a user. Thereafter, the client application updates the augmented reality GUI display 1400 to include a graphical overlay 1404 that includes a graphical representation of guidance information to facilitate the patient performing the first action in the sequence of actions required to set the active insulin time. For example, the illustrated guidance information 1404 indicates the patient needs to navigate the user input selection through the menu or list presented on the infusion device GUI display 1410 to select the "Options" menu element from within the list. In various embodiments, in addition or in alternative to text, the guidance overlay 1404 could include images, video, animation, and/or the like. The guidance overlay 1404 may also be augmented by auditory feedback, which could include an audio representation of the guidance information 1404 generated using text-to-speech functionality. In yet other embodiments, the guidance information 1404 could include a translation of the text depicted on the captured infusion device GUI display 1410 into a different language and/or auditory feedback of a translation of the text depicted on the captured infusion device GUI display 1410 could be provided to support a patient or user's preferred language.

In exemplary embodiments, the graphical overlay 1404 is positioned within the augmented reality GUI display 1400 on the display associated with the mobile device 1000 and with respect to the graphical representation of the infusion device 1100 such that it is adjacent to the graphical representation of the infusion device GUI display 1410. For example, the control module and/or client application at the mobile device 1000 may analyze the captured image to identify or otherwise determine the coordinate location for where the infusion device GUI display 1410 will be depicted on the display device of the mobile device 1000, and then generate the graphical overlay 1404 visually overlying nearby coordinates of the depicted image 1402 such that the graphical overlay 1404 is adjacent to the infusion device GUI display 1410. In this regard, a three-dimensional position and orientation of the infusion device 1100 (or a point of interest on the infusion device 1100) may be determined, which, in turn, may be utilized as a reference for positioning the graphical overlay 1404 relative to the reference position (e.g., by assigning a three-dimensional position and orientation to the guidance overlay 1404 based on the reference). For example, in the illustrated embodiment, the guidance overlay 1404 is provided at or along the top edge of the main menu GUI display 1410. In one or more embodiments, the guidance overlay 1404 is effectively stuck to the infusion device 1100, such that as the location of the infusion device 1100 within the background imagery 1402 changes, the position of the guidance overlay 1404 changes in a corresponding manner to dynamically update in real-time and maintain a fixed spatial relationship with respect to the infusion device GUI display 1410. That said, in other embodiments, the position or orientation of the guidance overlay 1404 could be independent of the position or orientation of the infusion device 1100.

Referring now to FIG. 15, after the patient navigates through the menu on the infusion device GUI display 1410 to select the "Options" menu element as indicated by the guidance overlay 1404, the infusion device 1100 generates an updated GUI display 1510 that depicts a list of menu elements associated with the "Options" menu. In response to the change to the captured GUI display on the infusion device 1100, the client application utilizes image recognition or other image processing techniques to map or otherwise correlate the updated GUI display 1510 to the options menu GUI display, and then determines what the next action within the sequence that the user needs to take in order to arrive at a GUI display from the options menu GUI display that will ultimately allow the active insulin time to be set or adjusted by a user. Thereafter, the client application updates the augmented reality GUI display 1500 to include an updated graphical overlay 1504 that reflects updated guidance information to facilitate the patient performing the next action in the sequence of actions required to set the active insulin time. For example, the illustrated guidance information 1504 indicates the patient needs to navigate the user input selection through the options menu GUI display 1510 to select the "Delivery Settings" menu element from within the list. Again, the guidance overlay 1504 may be positioned within the augmented reality GUI display 1500 on the display associated with the mobile device 1000 such that it is adjacent to, and maintains a fixed spatial relationship with respect to, the underlying graphical representation 1502 of the options menu GUI display 1510.

Referring now to FIG. 16, after the patient has navigated through the sequence of actions to arrive at the infusion device GUI display 1610 that allows the active insulin time to be set or adjusted, the client application utilizes image recognition or other image processing techniques to map or otherwise correlate the infusion device GUI display 1610 to the active insulin time GUI display. Based on the active insulin time GUI display being currently presented and the previously-determined user objective of adjusting the active insulin time, the client application generates corresponding guidance information that explains how the patient can adjust the active insulin time. Thereafter, the client application generates an updated augmented reality GUI display 1600 on the mobile device 1000 that includes a graphical representation of the generated guidance information 1604 for adjusting the active insulin time that overlies the graphical representation 1602 of the infusion device 1100 in a manner that allows the patient to concurrently view the guidance information 1604 while adjusting the active insulin time. After the patient adjusts the active insulin time, the patient-specific active insulin time value may be stored or otherwise maintained onboard the infusion device 1100 in lieu of the previous active insulin value, and thereby influencing subsequent operation of the infusion device 1100 when any autonomous operating modes, bolus wizards, or other features referencing the active insulin time parameter are utilized.

Figure 17:
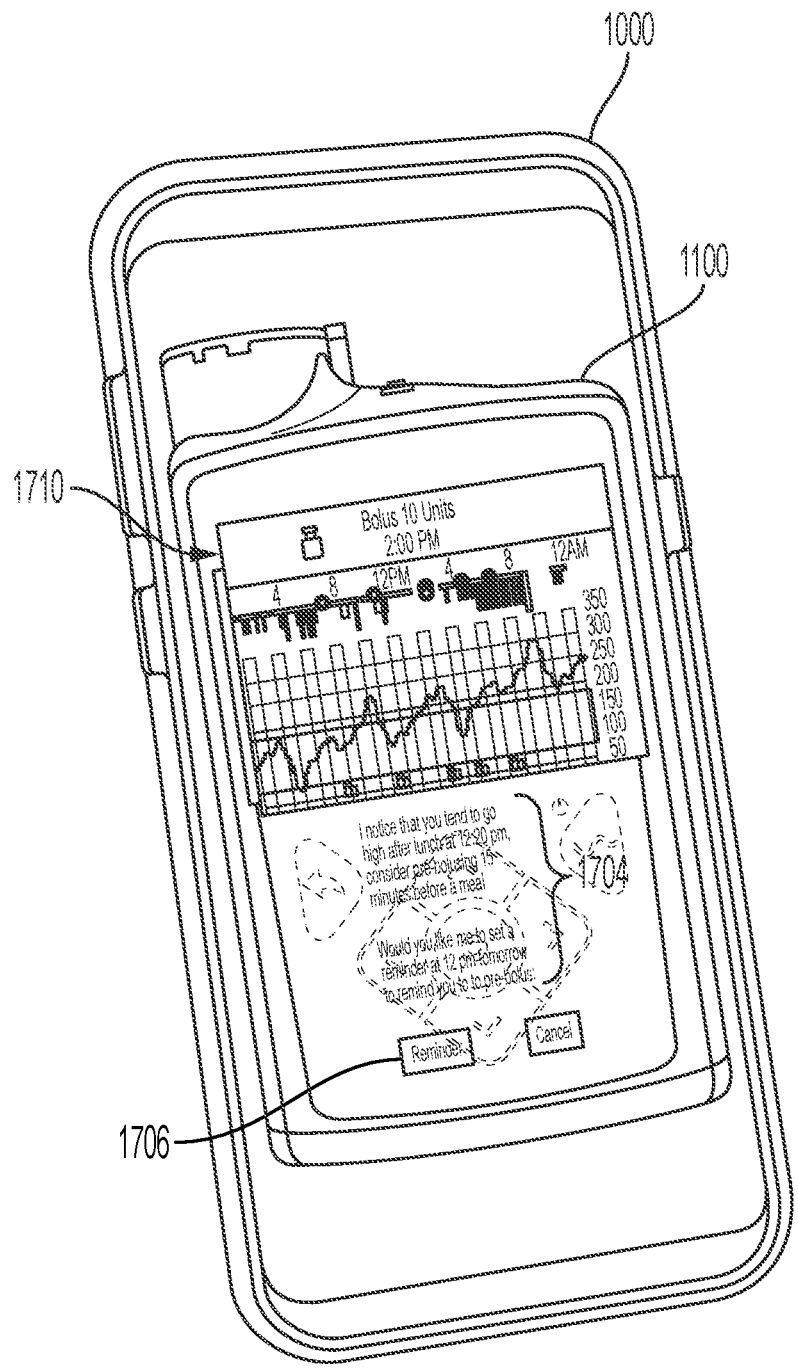

FIG. 17 depicts yet another example of the augmented reality guidance process 900 of FIG. 9 providing guidance pertaining to the current GUI display presented on the infusion device 1100. In the embodiment of FIG. 17, the infusion device GUI display 1710 depicts a graph of historical data associated with the patient (e.g., historical measurement data, historical bolus data, historical meal data, and/or the like). Based on recognizing the current infusion device GUI display 1710 as a patient monitoring GUI display depicting historical data associated with the patient and the user objective of understanding the current GUI display, the client application at the mobile device 1000 generates guidance information pertaining to the patient's historical data. In this regard, the client application at the mobile device 1000 may obtain historical glucose measurement data, historical insulin delivery data, historical bolus data, historical meal data, and the like from one or more other components 702, 704, 714, 716 of the patient management system 700, and then analyze the patient's historical data to generate guidance information that explains the patient's historical data depicted on the infusion device GUI display 1710.

For example, the client application at the mobile device may calculate or otherwise determine one or more metrics that summarize or otherwise characterize the patient's historical measurement data, such as a percentage of time the patient's glucose measurement values were within a predefined range of values (e.g., a percentage time in range between 80 mg/dL and 170 mg/dL), a percentage of time the patient's glucose measurement values were above and/or below a threshold (e.g., a percentage of time below 80 mg/dL, a percentage of time above 170 mg/dL, and the like), an average glucose measurement value, and/or the like. Thereafter, a guidance overlay may be provided on the mobile device 1000 that includes such metrics that summarize glucose measurement values that may be depicted on a graph on the mobile device 1000, thereby augmenting the GUI display on the mobile device 1000 by providing additional guidance or explanatory information that could not otherwise be presented on the mobile device 1000 concurrently with the measurement data due to the limited display size or other constraints at the medical device 1100.

In the illustrated embodiment, the client application at the mobile device analyzes the patient's historical data to identify a behavior or event pattern based on the historical data and generates a guidance overlay 1704 that identifies the detected pattern and provide explanatory information and other guidance. For example, the illustrated guidance overlay 1704 identifies detection of a postprandial hyperglycemic event pattern and includes a recommended or suggested remedial action that the patient could consider to mitigate the postprandial hyperglycemic event pattern. Additionally, the illustrated guidance overlay 1704 includes a selectable GUI element 1706 that the patient may select to configure the infusion device 1100 and/or the mobile device 1000 to facilitate or implement the recommended remedial action. For example, selection of the GUI element 1706 may cause one of the devices 1000, 1100 to automatically set or otherwise configure a reminder or other user notification to be automatically generated by one of the devices 1000, 1100 at or around a time associated with the detected event pattern. In other embodiments, selection of the GUI element 1706 may result in an adjustment to one or more of the current infusion device settings. For example, in some embodiments, selection of the GUI element 1706 could result in the client application at the mobile device 1000 configuring the infusion device 1100 to automatically and autonomously deliver an insulin bolus at or around a time associated with the detected event pattern.

It should be noted that the embodiments depicted in FIGS. 10-17 are provided for purposes of explanation and are not intended to be limiting. In this regard, practical embodiments of the augmented reality guidance process 900 could provide any number of different forms or combinations of guidance information overlays with respect to any number of different GUI displays that may be presented on any sort of medical device. Moreover, while FIGS. 10-17 depict examples of augmented reality displays depicted on a smartphone or similar type of mobile device, it should also be appreciated that the augmented reality guidance process 900 could provide such guidance overlays in an equivalent manner using smartglasses, head-mounted or head-wearable devices, or the like. It will be appreciated that in such embodiments where the display element of the device is effectively transparent, graphical representations of the imagery captured by the imaging device need not be projected or otherwise displayed on the display element. That said, the position of the medical device with respect to the head-worn device may still be determined (e.g., based on the knowledge of the orientation and position of the imaging device with respect to the display element), thereby allowing the guidance overlays to be provided adjacent to the medical device and spatially fixed with respect to the medical device in a similar manner as described above.

In some embodiments, captured images may be transmitted or otherwise uploaded to a remote device (e.g., remote device 714) or other remote support personnel to facilitate human-assisted troubleshooting. For example, captured images may be provided to remote support to allow remote support personnel to concurrently view the current state of the patient's medical device substantially in real-time, thereby improving the efficacy of remote troubleshooting. Captured images can also be uploaded and analyzed at a remote device to perform data analytics with respect to users' interactions with the medical device. For example, analyzing captured images across different users may allow for the most troublesome GUI displays or medical device states to be identified, or using the timestamps associated with captured images, it may be determined which GUI displays require the most time for users to navigate or troubleshoot. Thus, a designer may isolate poorly performing GUI displays and identify which GUI displays may require redesign or modifications.

Behavioral Recommendations Using Augmented Reality

Figure 18:
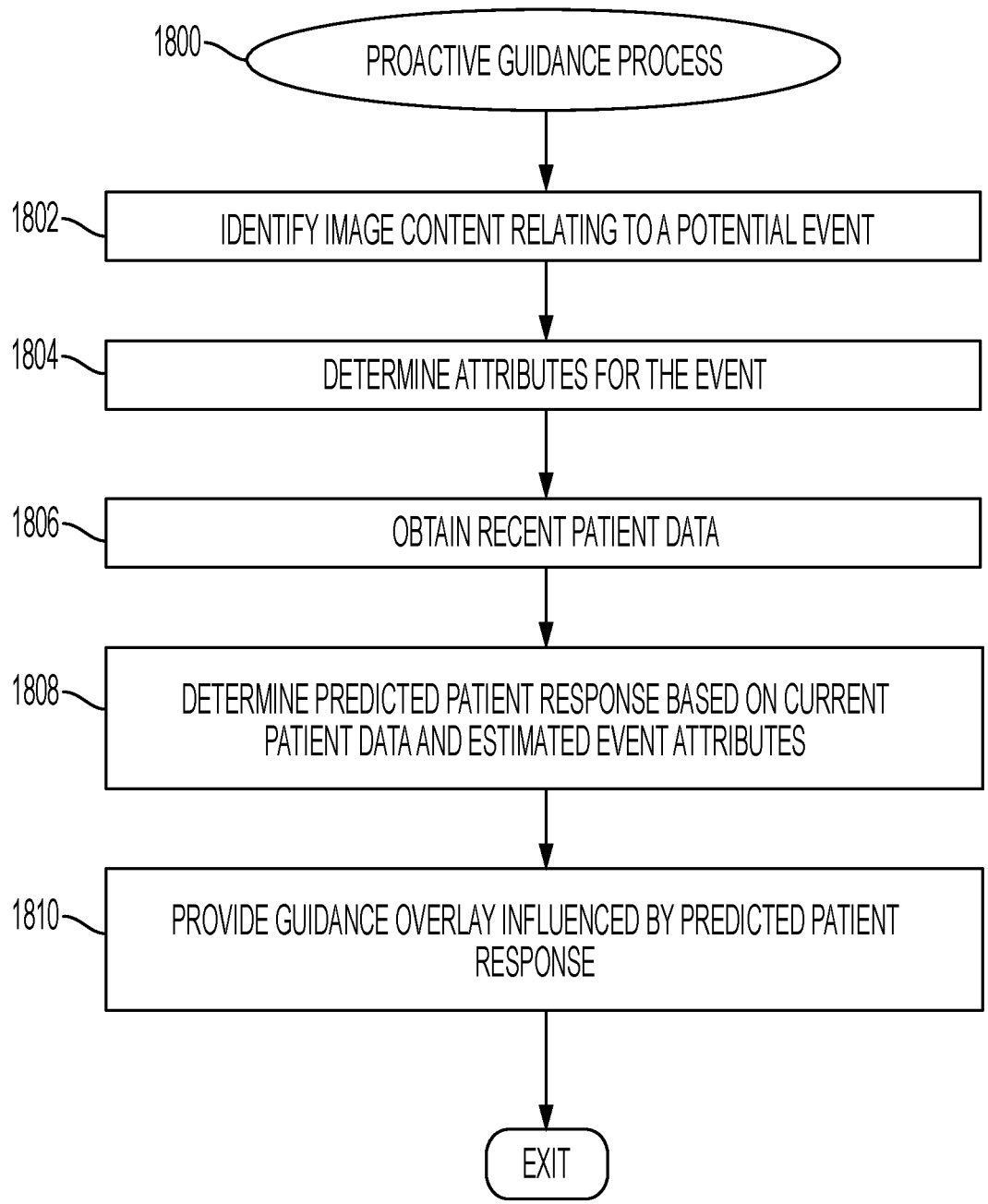
FIG. 18 is a flow diagram of an exemplary proactive guidance process in one or more exemplary embodiments.
Figure 19:
FIGS. 19-20 depict exemplary embodiments of augmented reality GUI displays suitable for presentation by an electronic device in connection with the proactive guidance process of FIG. 18.
Figure 20:
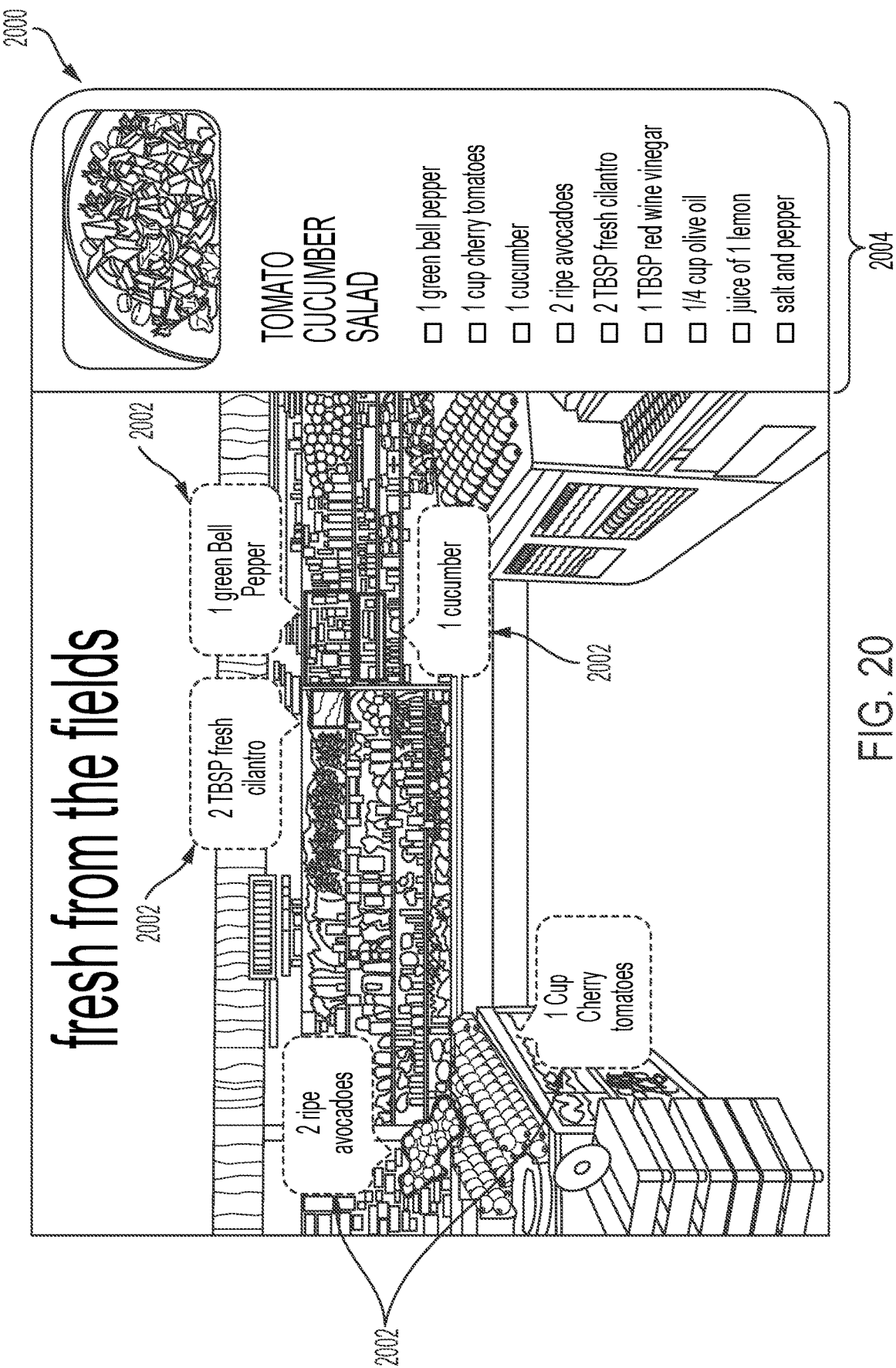

Referring now to FIGS. 18-20, in one or more exemplary embodiments, augmented reality is utilized to visually overlay recommendations or other guidance based on the patient's predicted physiological response in the future to content in a captured image. In this regard, a patient may be provided recommendations or guidance in real-time regarding how potential behaviors (e.g., meals, exercise, medication, sleep, or the like) may influence the patient's physiological response, and thereby proactively improve management of the his or her condition through more informed decision making. Additionally, the recommendations or guidance may be presented in a nondisruptive manner using augmented reality, thereby minimizing the potential distraction or interference with respect to the patient's current activity or behavior.

FIG. 18 depicts an exemplary proactive guidance process 1800 for providing real-time guidance to a patient regarding potential events or behaviors that the patient could engage in. The various tasks performed in connection with the proactive guidance process 1800 may be performed by hardware, firmware, software executed by processing circuitry, or any combination thereof. For illustrative purposes, the following description refers to elements mentioned above in connection with FIGS. 1-8. For purposes of explanation, the proactive guidance process 1800 may be described herein primarily in the context of being implemented at a client device 706, 800 in a patient management system 700. It should be appreciated that the proactive guidance process 1800 may include any number of additional or alternative tasks, the tasks need not be performed in the illustrated order and/or the tasks may be performed concurrently, and/or the proactive guidance process 1800 may be incorporated into a more comprehensive procedure or process having additional functionality not described in detail herein. Moreover, one or more of the tasks shown and described in the context of FIG. 18 could be omitted from a practical embodiment of the proactive guidance process 1800 as long as the intended overall functionality remains intact.

The proactive guidance process 1800 begins by detecting or otherwise identifying content in a captured image that corresponds to a particular type of lifestyle event that that patient could engage in that might influence the patient's physiological condition (task 1802), such as, for example, a meal, exercise, or the like. In this regard, in some embodiments, where the computing device 706, 800 implementing the proactive guidance process 1800 is realized as smartglasses or another head-worn device where the imaging device 808 continually captures images, the control module 802 may continually analyze and monitor the captured images output by the imaging device 808 to recognize or identify one or more items that correspond to a lifestyle event (e.g., an item of food, an exercise machine, or the like). In other embodiments, the proactive guidance process 1800 may begin in response to the patient manipulating the computing device 706, 800 to operate the imaging device 808 and capture an image of something that the patient would like guidance or recommendations with respect to.

After identifying content corresponding to a lifestyle event, the proactive guidance process 1800 continues by calculating, estimating, or otherwise determining one or more attributes to be assigned to the lifestyle event (task 1804). For example, if the captured content includes an item of food, the control module 802 may analyze the captured image of the food item to identify or otherwise determine the type of food item depicted and estimate the physical dimensions of the food item. As one example, to estimate physical dimensions of a captured food item, the control module 802 utilize image recognition detect points in space corresponding to the food item, and then utilize output from inertial sensors of the computing device 706, 800 to determine the approximate distance and/or location of the food item relative to the computing device 706, 800, and thereby estimate the dimensions of the food item. Image recognition or other machine learning may also be utilized to match the captured food item to a particular type of food.

Based on the type of food item, in one or more embodiments, the control module 802 may access the memory 810 or a remote device 714, 716 to retrieve reference data or information indicative of the nutritional content or characteristics associated with that type of food on a per unit basis, and then utilize the estimated physical dimensions to convert the reference data into a corresponding estimate of the nutritional content associated with the item of food depicted in a captured image. For example, the remote device 714 and/or the database 716 may store nutritional information associated with different types of meals or nutritional content, such as, for example, a serving size or unit, the amount of carbohydrates per serving size, the amount of fat per serving size, the amount of protein per serving size, the amount of calories per serving size, the amount of fiber per serving size, the amount of sodium per serving size, and the like. An application at a client device 706, 800 may retrieve or otherwise request the nutritional information associated with the current meal content from the remote device 814, and then utilize the nutritional information and the estimated meal size to calculate or determine a complete nutritional profile for the meal being consumed. In this manner, the amount of carbohydrates, fat, protein, fiber, sugar, or other nutritional attributes associated with a potential meal may be determined based on the captured image. In other embodiments, the control module 802 may access the memory 810 or a remote device 714, 716 to retrieve historical meal data associated with the patient to identify historical meal events for the patient that included the identified type of food, and then calculate or otherwise determine estimated nutritional attributes in a patient-specific manner based on the subset of the patient's historical meal data including that type of food (e.g., by averaging the carbohydrates, fat, protein, sugar, or the like associated with similar historical meals). In yet another example, where the captured content includes a menu describing or depicting an item of food, the content of the menu may be analyzed to derive the nutritional information from the captured image of the menu, as described in greater detail below in the context of FIG. 20.

As yet another example, where the captured content includes an exercise machine, the control module 802 may access the memory 810 or a remote device 714, 716 to identify previous exercise events for the patient that correspond to that type of exercise and then utilize the historical measurement data or other historical event log data associated with those previous instances of exercise to determine estimated attributes for a potential exercise event. For example, historical acceleration data, historical heart rate measurement data, or the like may be utilized to calculate or otherwise determine an estimated exercise intensity and/or an estimated exercise duration for the patient in a patient-specific manner based on the patient's historical exercise events. Various examples of predicting patient behaviors or activities are described in U.S. patent application Ser. No. 15/847,750.

Still referring to FIG. 18, after assigning attributes to the content captured in the image, the proactive guidance process 1800 continues by receiving or otherwise obtaining recent patient data and calculating or otherwise determining a predicted physiological response by the patient to the potential lifestyle event identified within the captured image based on the attributes assigned to that lifestyle event and the patient's recent measurement data, event log data, and the like (tasks 1806, 1808). For example, the computing device 706, 800 may obtain from one or more of the sensing arrangements 104, 404, 406, 408, 704, the infusion device 102, 200, 402, 702 and/or the database 716 the current or most recent sensor glucose measurement values associated with the patient, along with data or information quantifying or characterizing recent insulin deliveries, meals, exercise, and potentially other events, activities or behaviors by the user within a preceding interval of time (e.g., within the preceding 2 hours). In some embodiments, the computing device 706, 800 may also obtain data or information quantifying or characterizing the current or recent operational contexts associated with the infusion device 102, 200, 402, 702. Thereafter, the control module 802 may obtain from memory 810 or a remote database 716 one or more prediction models associated with the patient and input or otherwise provide the recent patient data and the estimated event attributes into the prediction model(s) to calculate or otherwise obtain a predicted physiological response by the patient. Various examples of predicting or forecasting future glucose levels for a patient using patient-specific prediction models are described in U.S. patent application Ser. No. 15/933,264 and U.S. patent application Ser. No. 16/137,386.

After determining the predicted physiological response by the patient to the captured content, the proactive guidance process 1800 generates or otherwise provides a graphical overlay proximate to the captured content using augmented reality that includes information or other indicia that are influenced by the predicted physiological response (task 1810). For example, a graphical overlay may be provided visually overlying or adjacent to captured content corresponding to a lifestyle event that indicates how much a patient's glucose levels are predicted to rise or fall if that lifestyle event corresponding to the captured image is engaged in by the patient in the predicted manner. As another example, the graphical overlay may be utilized to effectively tint or shade the captured content using a visually distinguishable characteristic that indicates whether or not the lifestyle event would have a positive or negative impact on the patient's physiological condition. For example, if the predicted response to the lifestyle event is expected to result in a decrease in the patient's percentage time in range, an increase the difference between the patient's glucose level and a target glucose level, or result in a hyperglycemic, hypoglycemic or other adverse event, a transparent (or semi-transparent) graphical overlay having a solid color indicative of an adverse outcome (e.g., red) may be presented overlying the corresponding content using augmented reality. Conversely, if the predicted response to the lifestyle event is expected to result in an increase in the patient's percentage time in range, reduce the difference in the patient's glucose level relative to a target glucose level, or otherwise improve the patient's glucose levels, a transparent (or semi-transparent) graphical overlay having a different color indicative of a positive outcome (e.g., green) may be presented overlying the corresponding content using augmented reality. The graphical overlay may also include the attributes assigned to the lifestyle event that were estimated, predicted, or otherwise determined based on the captured content and/or the patient's historical data. Additionally, in some embodiments, the predicted response may be utilized to generate additional guidance information that may be presented as part of or in conjunction with the graphical overlay. For example, if the predicted response to the lifestyle event results in a predicted glucose level above some threshold value, the attributes assigned to the lifestyle event and/or the predicted glucose level may be utilized to calculate or otherwise determine a recommended bolus amount of insulin to be administered in conjunction with the lifestyle event, which, in turn, may be presented within the graphical overlay along with providing graphical indication of the predicted glycemic response.

FIG. 19 depicts an exemplary embodiment of an augmented reality GUI display 1900 suitable for presentation in connection with the proactive guidance process 1800 of FIG. 18. In this regard, FIG. 19 depicts an embodiment where the content captured by the imaging device is realized as a menu that contains a list of potential food items or meal configurations that the patient may be considering ordering (e.g., task 1802). In the illustrated embodiment, the proactive guidance process 1800 analyzes the menu to select or otherwise identify potential meal events for analysis from within the menu. In this regard, in some embodiments, the proactive guidance process 1800 may exhaustively analyze each item or entry from the menu, while in other embodiments, the proactive guidance process 1800 may analyze the patient's historical meal event data to select only those meal items that the patient is likely to be interested in based on the patient's historical meal behavior. For example, a probability metric may be calculated or otherwise determined based on the patient's historical meal data for each menu item to assign values indicative of the relative probability or likelihood of the patient ordering the respective menu item.

Thereafter, only those menu items having sufficiently high probability values may be further analyzed by the proactive guidance process 1800.

For each menu item being analyzed, the proactive guidance process 1800 determines attributes representative of the nutritional content of the menu item before determining a predicted patient response to the respective menu item (e.g., task 1804). For example, the menu text may be analyzed using optical character recognition to identify the name or other indicia of the food type associated with the respective menu item, which, in turn may be utilized to retrieve reference data or information indicative of the nutritional content or characteristics associated with that type of food on a per unit basis, and then calculate or otherwise determine attributes for the meal based on those nutritional characteristics. In other embodiments, the patient's historical meal event data may be analyzed to identify previous instances of similar meals, with the data associated with those previous instances being averaged or otherwise analyzed to obtain representative attributes for that type of meal (e.g., by averaging the amount of carbohydrates associated with previous meals, etc.). In yet other embodiments, the nutritional content or other attributes associated with the menu item may be printed on or otherwise provided from within the menu and identified based on the captured image(s) of the menu, or by querying or searching nutritional data associated with a restaurant that is available from a remote location over a network.

The attributes assigned to a respective menu item are then input or otherwise provided to a glucose forecasting model associated with the patient along with recent glucose measurement data, insulin delivery data, and/or the like for the patient to arrive at a forecasted glucose value likely to result from consuming the respective menu item (e.g., tasks 1806, 1808). The forecasted glucose value may then be stored or otherwise maintained in association with the respective menu item and utilized to populate or otherwise provide graphical overlays that visually overlie the menu. In the illustrated embodiment, the proactive guidance process 1800 identifies the menu items that achieve the best physiological outcome for the patient, and then generates graphical overlays proximate to those menu items to recommend or suggest menu items for ordering by the patient. For example, a graphical overlay 1902 may be provided visually overlying the menu proximate the "Pesto Chicken Melt" menu item to visually indicate to the patient that menu item is recommended for optimizing the patient's glucose management. In this regard, the graphical overlay 1902 includes text indicating that the menu item would be a good choice, along with indicating the patient's forecasted glucose value associated with that menu item. Additionally, other attributes associated with the menu item may be provide, such as, for example, estimated amounts of carbohydrates, fat, protein, sugar, or the like that were determined or otherwise assigned to the menu item (e.g., task 1804). Other information, such as estimated or recommended bolus amounts, may also be provided in the graphical overlay 1902. In the illustrated embodiment, a second graphical overlay 1904 is provided visually overlying the menu proximate the "Veggie Quiche" menu item to visually indicate the forecasted glucose value associated with that menu item, the nutritional attributes associated with the menu item, and/or the like.

As illustrated, the graphical overlays 1902, 1904 may be viewed by the patient while the patient is concurrently viewing or analyzing the menu, thereby facilitating the patient with making healthy meal choices to proactively manage his or her glucose levels. In addition to the guidance overlays 1902, 1904, additional graphical overlays 1906, 1908 that highlight or distinguish the recommended menu items may also be provided. For example, transparent (or semi-transparent) highlight regions 1906, 1908 may be presented visually overlying the menu items in a color or other visually distinguishable characteristic that indicates a positive outcome is predicted for the patient (e.g., a green color). In the illustrated embodiment, the guidance overlays 1902, 1904 include a pointer or otherwise emanate from the highlight regions 1906, 1908, thereby facilitating the patient establishing a mental association between the information depicted within the guidance overlays 1902, 1904 and the recommended items on the menu. Additionally, in exemplary embodiments, the graphical overlays 1902, 1904, 1906, 1908 maintain a fixed spatial relationship with respect to the menu such that they are effectively stuck to their respective menu items associated therewith. For example, based on the orientation and position of the imaging device with respect to the display element and/or the viewer's head or eyes, the relative real-world position of the menu items may be determined based on the captured image(s), and then utilized to position the guidance overlays with respect to the determined position of the menu items. Thus, as the menu item moves within the patient's field of view, the graphical overlays 1902, 1904, 1906, 1908 may be effectively anchored to the menu and move in a corresponding manner to maintain the visual association with their associated menu items.

In some embodiments, the graphical overlay may summarize or characterize the patient's history or prior behaviors in a similar context, for example, by reviewing past meal choices or amounts and the corresponding glycemic outcomes. Additionally, the subject matter described herein is not limited to providing guidance regarding meals or boluses, but may also include recommendations or suggestions regarding sleep, exercise, medications, and/or the like. In some embodiments, the captured image may be modified or otherwise altered (e.g., to highlight recommended or disfavored options), with the modified image being provided as feedback to the patient. Additionally, while the subject matter of the proactive guidance process 1800 may be primarily described in connection with meals, it could be implemented in an equivalent manner for medications. For example, based on a captured image of the patient's medications (or a subset thereof), the proactive guidance process 1800 may analyze the patient's recent medication intake, the patient's recent measurement and/or delivery data, and/or the like to provide guidance regarding which (if any) medications should be taken and corresponding dosage amounts.

FIG. 20 depicts another exemplary embodiment of an augmented reality GUI display 2000 suitable for presentation in connection with the proactive guidance process 1800 of FIG. 18. In this regard, FIG. 20 depicts an embodiment where the proactive guidance process 1800 analyzes the surrounding environment within a grocery store to identify different potential food items within the patient's field of view and analyze those items to identify or otherwise determine recommended food items based on the patient's predicted physiological response(s) to different food items or combinations thereof. Graphical overlays 2002 may then be generated or otherwise provided that visually overlie the environment within the patient's field of view to highlight or otherwise indicate recommended food items, recommended quantities of those food items, and/or the like. Additionally, in some embodiments, the set of recommended food items within the current field of view may be utilized to search or otherwise query a recipe database (e.g., maintained in local memory or at a remote database) to identify a suggested recipe that includes one or more of the recognized and recommended food items. A recipe graphical overlay 2004 may then be generated or otherwise provided at or along an edge of the display such that it only obstructs the underlying environment at the periphery of the patient's field of view. Again, the patient may view the recommended food items and recipe suggestions while the patient is concurrently viewing and moving within the surrounding environment which reduces the disruption or burden on the patient with respect to obtaining recommendations or notifications while simultaneously facilitating a patient making healthier or more informed choices based on his or her predicted physiological response. Thus, the mental burden or stress for a patient collecting items for preparing a meal that supports his or her therapy is reduced. the user. In this regard, it should be noted that guidance overlays may also provided during preparation of a subsequent meal (e.g., by sequentially presenting recipe steps using augmented reality) to further reduce the patient burden.

Proactive Delivery Adjustments Based on Captured Images

Referring now to FIGS. 21-22, in one or more exemplary embodiments, the content in a captured image is utilized to proactively adjust delivery of fluid by an infusion device to account for the patient's predicted physiological response in the future to the content. For example, the patient consuming a meal may be recognized or otherwise identified based on one or more captured images, which, in turn may be utilized to deliver a bolus of insulin or adjust one or more settings or control parameters for an autonomous operating mode to account for the meal event captured within the image(s). Accordingly, delivery adjustments may be automatically or autonomously performed in a nondisruptive manner that minimizes the patient burden or other interference with respect to the patient's current activity or behavior.

FIG. 21 depicts an exemplary proactive delivery adjustment process 2100 for providing real-time delivery adjustments for a patient based on captured images. The various tasks performed in connection with the proactive delivery adjustment process 2100 may be performed by hardware, firmware, software executed by processing circuitry, or any combination thereof. For illustrative purposes, the following description refers to elements mentioned above in connection with FIGS. 1-8. For purposes of explanation, the proactive delivery adjustment process 2100 may be described herein primarily in the context of being implemented at a client device 706, 800 in a patient management system 700. It should be appreciated that the proactive delivery adjustment process 2100 may include any number of additional or alternative tasks, the tasks need not be performed in the illustrated order and/or the tasks may be performed concurrently, and/or the proactive delivery adjustment process 2100 may be incorporated into a more comprehensive procedure or process having additional functionality not described in detail herein. Moreover, one or more of the tasks shown and described in the context of FIG. 21 could be omitted from a practical embodiment of the proactive delivery adjustment process 2100 as long as the intended overall functionality remains intact.

The illustrated embodiment of the proactive delivery adjustment process 2100 begins by detecting or otherwise identifying content in a captured image that corresponds to a particular type of lifestyle event that that patient is or will likely be engaging in that could influence the patient's physiological condition and then calculating, estimating, or otherwise determining one or more attributes to be assigned to the lifestyle event (tasks 2102, 2104). In this regard, similar to the proactive guidance process 1800 described above, the control module 802 may continually analyze and monitor the captured images output by the imaging device 808 to recognize or identify one or more items that correspond to a lifestyle event, or begin in response to the patient manipulating the computing device 706, 800 to operate the imaging device 808 and capture an image. For example, a bolus wizard or similar feature of a client application executing on the computing device 706, 800 could be configured to receive a captured image of a meal in lieu of having a patient input counted carbohydrates or other parameters characterizing the meal. Again, similar to the proactive guidance process 1800, depending on the embodiment, estimated attributes may be assigned to the lifestyle event based on analysis of the captured image(s) and/or analysis of the patient's historical data corresponding to the particular type of lifestyle event identified from the captured image(s).

Still referring to FIG. 21, based on the attributes assigned to the lifestyle event identified from the captured image, the proactive delivery adjustment process 2100 calculates or otherwise determines a delivery adjustment to be implemented by the patient's infusion device (task 2106). For example, in one or more embodiments, a bolus amount of insulin to be delivered may be determined based on the assigned attributes (e.g., estimated carbohydrates or the like) to account for the patient's probable glycemic response to the lifestyle event. In this regard, bolus dosage amounts or bolus delivery schedules may be determined or otherwise adjusted in a manner that accounts for the predicted postprandial glycemic response to the nutritional content of the meal captured by the imaging device. In yet other embodiments, closed-loop control information or other settings or configuration data associated with an autonomous operating mode may be adjusted to account for the lifestyle event. After determining the delivery adjustment, the proactive delivery adjustment process 2100 instructs, commands, or otherwise configures the infusion device associated with the patient to automatically adjust fluid delivery to deliver fluid in accordance with the delivery adjustment (task 2108). In this regard, depending on the embodiment, the delivery adjustment may be determined at a client device 706, 800 and subsequently provided to the infusion device 702, while in other embodiments, indication of the lifestyle event and estimated attributes associated therewith are provided to the infusion device 702, which, in turn, automatically determines the appropriate delivery adjustments and configures itself accordingly.

For example, when the captured image includes meal content that consists of more fast acting carbohydrates relative to the amount of fat, fiber, or the like (e.g., a sugary or high carbohydrate breakfast), a bolus dosage amount determined by multiplying the estimated carbohydrate amount by a carbohydrate ratio may be scaled up by a factor greater than one to increase the meal bolus amount while also commanding, signaling, or otherwise instructing the command generation application 510 to temporarily suspend delivery by the closed-loop control system 500. Conversely, for meal content that consists of more fat relative to the amount of carbohydrates, the bolus dosage amount determined by multiplying the estimated carbohydrate amount by a carbohydrate ratio may be scaled by a factor less than one to decrease the meal bolus amount while also commanding, signaling, or otherwise instructing the command generation application 510 to temporarily utilize a lower target glucose value 602 and/or increase the minimum and/or maximum basal rate settings to gradually increase insulin delivery during the postprandial period to better account for the meal content. It should be noted that the manner or amount of adjustments to the bolus dosage amount or postprandial closed-loop control adjustments may be personalized or patient-specific and influenced by relationships between the patient's historical postprandial sensor glucose measurements and insulin deliveries associated with historical meal events having common nutritional content. Various examples of delivery adjustments based on the nutritional content of a meal are described in U.S. patent application Ser. No. 15/847,750. Similar delivery adjustments may be performed in an equivalent manner to account for exercise or other lifestyle events that may be detected based on captured image(s).

In exemplary embodiments, the loop defined by tasks 2102, 2104, 2106 and 2108 repeats throughout the duration of time a delivery adjustment is being implemented or otherwise having an effect on the patient's physiological condition to dynamically adjust the delivery of fluid based on one or more subsequently captured images. For example, a patient may capture an image of his or her plate after a meal, which, in turn may be analyzed by the proactive delivery adjustment process 2100 to identify the type and amount of food remaining, and corresponding attributes associated therewith (e.g., tasks 2102, 2104). Thereafter, the proactive delivery adjustment process 2100 may calculate or otherwise determine one or more delivery adjustments based on a difference between the actual attributes associated with the meal and the attributes that were previously-assigned at or around the start of the meal. For example, if, based on the amount of food remaining in the captured image, the proactive delivery adjustment process 2100 determines that the patient consumed fewer carbohydrates than were initially estimated, the proactive delivery adjustment process 2100 may temporally increase the target glucose value 602 and/or decrease the minimum and/or maximum basal rate settings to counteract any previous delivery adjustments and/or decrease insulin delivery to reduce the likelihood of postprandial hypoglycemia. Conversely, if, based on the amount of food remaining in the captured image, the proactive delivery adjustment process 2100 determines that the patient consumed more carbohydrates than were initially estimated, the proactive delivery adjustment process 2100 may further decrease the target glucose value 602 and/or increase the minimum and/or maximum basal rate settings to supplement the previous delivery adjustments and increase insulin delivery to reduce the likelihood of postprandial hyperglycemia. In this manner, the proactive delivery adjustment process 2100 may dynamically adjust insulin delivery in real-time based on a succession or sequence of images to fine tune insulin delivery in an autonomous and automated manner without reliance on manual inputs or manual reconfiguration.

In exemplary embodiments, a graphical overlay or other indicia of the proactive delivery adjustments are presented to the patient using augmented reality. The proactive delivery adjustment process 2100 may generate or otherwise provide graphical overlays 2202, 2204, 2206 that are positioned proximate to different food items recognized within the captured image(s) and indicate the identified food type associated with those respective items along with the estimated attributes (e.g., estimated grams of carbohydrates, estimated calories, and the like) assigned to those items based on their expected nutritional content and physical size determined from analyzing the captured image(s). Based on the estimated attributes assigned to the individual food items, the proactive delivery adjustment process 2100 may calculate or otherwise determine cumulative attributes to be assigned to the meal. For example, the proactive delivery adjustment process 2100 may add the individual attributes for each food item that makes up the meal to determine an estimated carbohydrate amount for the meal of 65.1 grams of carbohydrates and 35 grams of fat. Thereafter, the proactive delivery adjustment process 2100 may automatically adjust the infusion device 702 associated with the patient to account for a prospective meal of 65.1 grams of carbohydrates and 35 grams of fat, for example by determining and/or scheduling bolus insulin deliveries, adjusting closed-loop control parameters or settings, and/or the like. In other embodiments, based on the combination of food items in the meal, the proactive delivery adjustment process 2100 may analyze the patient's historical meal data to identify previous instances of the same or similar meal, determine estimated or probable meal attributes based on the patient's historical meal data, and then adjust delivery accordingly. After the infusion device 702 is configured to implement the determined delivery adjustments, the proactive delivery adjustment process 2100 may generate or otherwise provide an additional graphical overlay 2210 at or near a periphery or edge of the patient's field of view to indicate to the patient that the infusion device 702 has been adjusted to account for the meal, thereby notifying the patient that he or she does not need to manually bolus for the meal or take other action.

As described above, the delivery adjustments may be dynamically adjusted to account for the actual amount of the meal consumed by the patient. For example, if a subsequent image indicates that the patient has consumed all of the salad and breaded pork but did not eat any French fries, the proactive delivery adjustment process 2100 may calculate or otherwise determine a net differential between the actual attributes associated with the meal and the originally estimated meal attributes of −48 grams of carbohydrates and −17 grams of fat. Based on the differential, the proactive delivery adjustment process 2100 may temporally increase the target glucose value 602, decrease the minimum and/or maximum basal rate settings, decrease gain coefficient values, or otherwise modify the parameters or settings associated with the closed-loop operating mode to counteract the initial delivery adjustment and decrease the amount or rate of insulin delivery to reduce the likelihood of postprandial hypoglycemia. It should be noted that the subject matter described herein is not limited to pre- and post-meal adjustments, and in practice, delivery adjustments could be dynamically updated throughout the meal as the patient eats based on successively captured images.

Still referring to FIG. 22, in some embodiments, the proactive delivery adjustment process 2100 may be performed concurrently to or otherwise in concert with the proactive guidance process 1800. For example, the proactive guidance process 1800 may calculate or otherwise determine optimal amounts of the food items from the captured image that achieve the best outcome for the patient based on the patient's predicted glycemic response (e.g., the amount of food that maximizes time in range, minimizes the difference between the forecasted glucose level and a target glucose level, and/or the like). Thereafter, the proactive guidance process 1800 may provide additional graphical overlays 2222, 2224, 2226 that visually overlie the different food items and emphasize, highlight or otherwise indicate the optimal portion sizes for the respective food items. For example, a transparent (or semi-transparent) green overlay region may be presented overlying the optimal portion sizes of the different food items to indicate the optimal portion size, while a different colored overlay region (e.g., a red color) may be presented visually overlying remaining portions of those food items to indicate suboptimal or potentially excessive consumption of those food items. In yet other embodiments, the proactive guidance process 1800 may be configured to graphically indicate the maximum portion sizes that can be consumed before increasing the risk of a future hyperglycemic event (e.g., a forecasted glucose level above a hyperglycemic threshold), or alternatively, the minimum portion sizes that should be consumed to limit the risk of a future hypoglycemic event or otherwise maintain the patient's future glucose levels above a minimum threshold glucose value.

In some embodiments, the proactive delivery adjustment process 2100 may utilize the estimated attributes corresponding to the optimal portion sizes indicated by the proactive guidance process 1800 for purposes of determining delivery adjustments under the assumption that the patient is likely to attempt to adhere to the guidance overlays. In such embodiments, one or more subsequent images may be captured and analyzed to identify deviations from the optimal portion sizes, and dynamically perform additional delivery adjustments to account for the deviation between the patient's actual meal behavior and the recommended meal behavior. It should be noted that there are any number of different ways the proactive guidance process 1800 and the proactive delivery adjustment process 2100 to facilitate improved management of the patient's glucose levels while simultaneously minimizing the burdens on the patient when it comes to real-time behavioral decision-making, configuration of his or her infusion device, and the like.

In some embodiments, captured images of the meal, both before and after the meal, may be stored and/or analyzed to provide a modified or combined image representative of the patient's behavior. For example, before and after images may be utilized to generate a modified image that represents the amount of food consumed by the patient. Such a modified image could be presented to the patient after the meal for review, or at or around the time of a subsequent meal to provide the patient with feedback regarding his or her portion control, previous meal behavior, and/or the like.

Medical Device Training Using Augmented Reality

Figure 23:
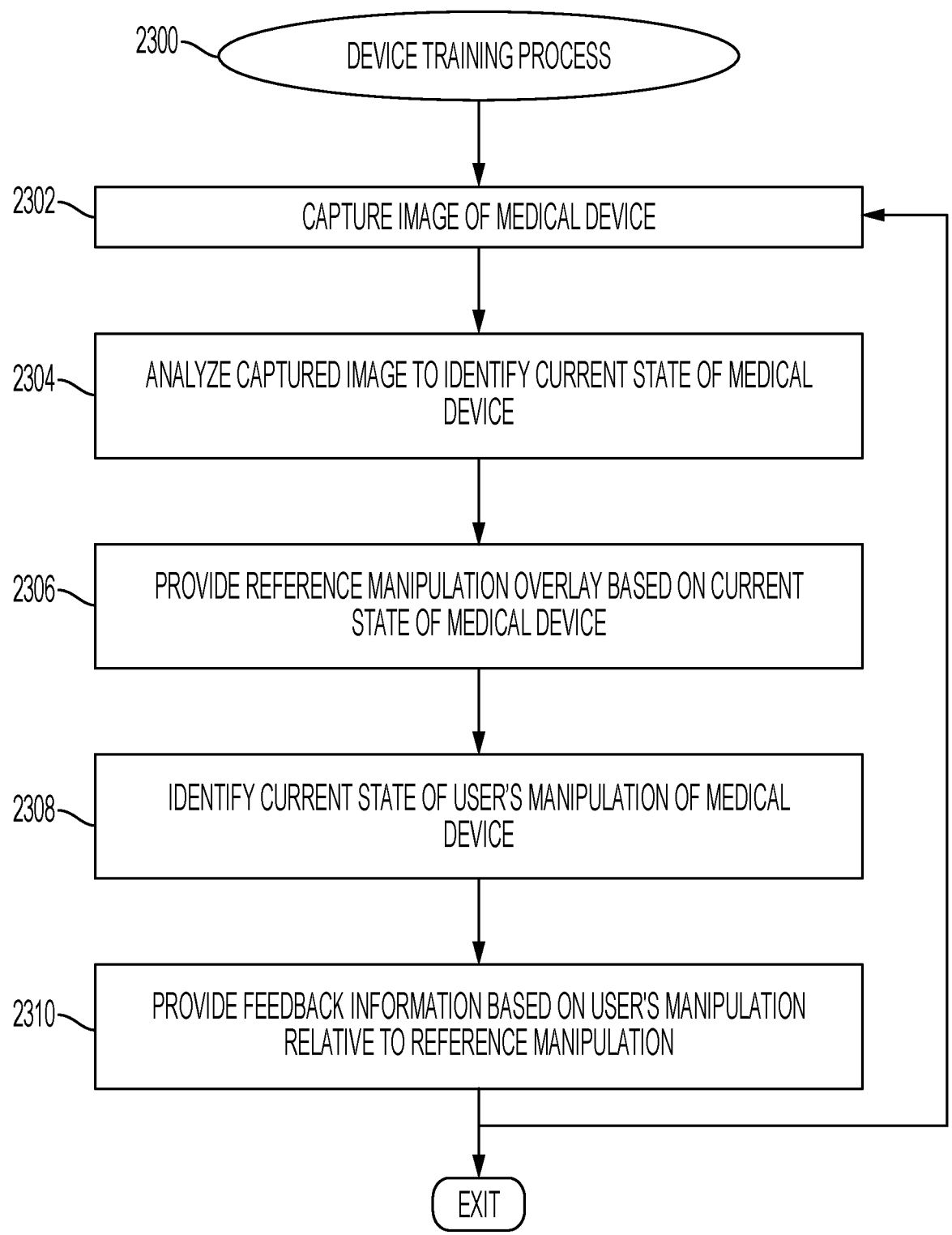
FIG. 23 is a flow diagram of an exemplary device training process in one or more exemplary embodiments.
Figure 24:
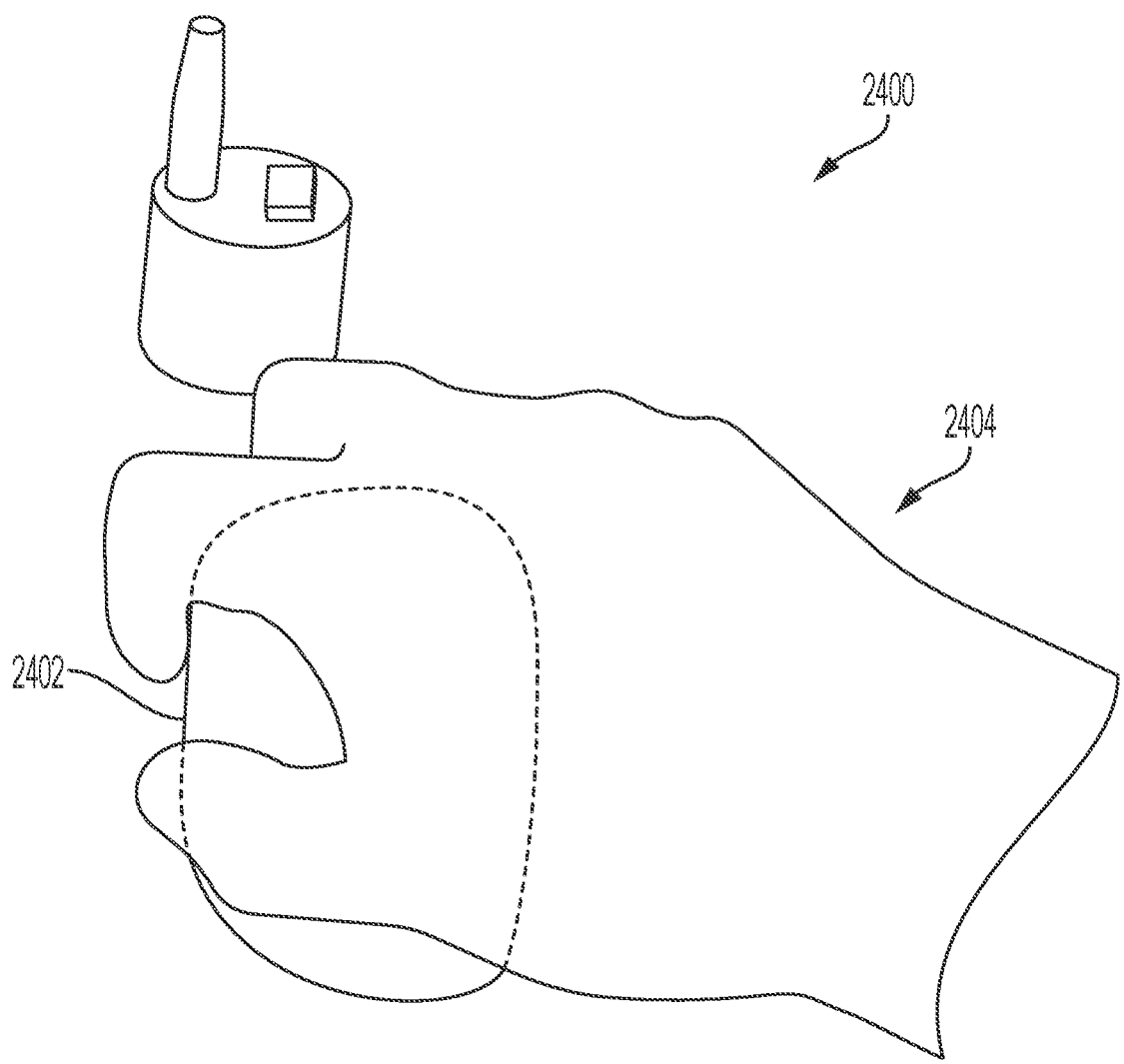
FIG. 24 is an exemplary augmented reality GUI displays suitable for presentation by an electronic device in connection with the device training process of FIG. 23.

Referring now to FIGS. 23-24, in one or more exemplary embodiments, augmented reality is utilized to visually overlay guidance for manipulating or otherwise interacting with a medical device to facilitate correct operation of the medical device by a user. In this regard, based on the observed current state of the medical device (e.g., the position, orientation, display state, and/or the like) identified based on captured images, a reference overlay may be generated or otherwise provided that provides a reference for manually interacting with the medical device in its currently observed state. A patient or other user may then concurrently view the reference overlay while manually interacting with the medical device to achieve a particular objective. In some embodiments, the observed state of the user's fingers, hand, or the like is also identified based on captured images and utilized to determine and provide feedback based on the relationship between the user's interaction with the medical device and the reference overlay. For example, guidance for reducing the differences or deviations between the observed hand position and a reference hand position may be provided, thereby improving the user's interaction with the medical device. In yet other embodiments, the user's interaction with the medical device may be scored or otherwise quantified based on the relationship between the user's interaction with the medical device and the reference overlay. In this manner, augmented reality may be utilized to train or otherwise instruct patients, healthcare providers, or other users using a medical device.

FIG. 23 depicts an exemplary device training process 2300 for providing guidance to a patient or user in real-time to facilitate achieving a desired operation of a medical device, such as infusion device 102, 200, 402, 702. The various tasks performed in connection with the device training process 2300 may be performed by hardware, firmware, software executed by processing circuitry, or any combination thereof. For illustrative purposes, the following description refers to elements mentioned above in connection with FIGS. 1-8. For purposes of explanation, the device training process 2300 may be described herein primarily in the context of being implemented at a client device 706, 800 in a patient management system 700. It should be appreciated that the device training process 2300 may include any number of additional or alternative tasks, the tasks need not be performed in the illustrated order and/or the tasks may be performed concurrently, and/or the device training process 2300 may be incorporated into a more comprehensive procedure or process having additional functionality not described in detail herein. Moreover, one or more of the tasks shown and described in the context of FIG. 23 could be omitted from a practical embodiment of the device training process 2300 as long as the intended overall functionality remains intact.

The device training process 2300 begins by capturing or otherwise obtaining one or more images of the medical device and analyzing or otherwise processing the image to identify the current state of the medical device (tasks 2302, 2304). In this regard, based on the analysis of the image(s) from the imaging device 808, the control module 802 identifies or otherwise determines the current position and/or orientation of the medical device 702 relative to the user. In some embodiments, the control module 802 also determines the current state of the GUI display presented at medical device 702. Thereafter, the device training process 2300 generates or otherwise provides a reference manipulation overlay for achieving a particular objective based on the current state of the medical device (task 2306). In this regard, the reference manipulation overlay indicates how a user should manipulate the medical device or otherwise position or orient his or her hands or fingers with respect to the medical device to facilitate achieving a particular objective. In some embodiments, the user's objective may be inferred or otherwise determined based on the current state of the medical device. For example, the current state of the medical device may indicate that the user is in the process of attempting to achieve a particular objective, or the current state of the medical device may indicate one or more steps that need to be performed with respect to the medical device to enable operation of the medical device. In yet other embodiments, the objective that the patient or user is trying to accomplish or achieve may be identified in response to a user input or other selection (e.g., via a client application at the electronic device 706, 800).

FIG. 24 depicts an exemplary embodiment of an augmented reality GUI display 2400 suitable for presentation in connection with the device training process 2300. Based on the current state of the medical device 2402 and the current objective, the control module 802 generates or otherwise provides a reference manipulation overlay 2404 overlying the medical device 2402 that indicates, to the user, how he or she should grasp or otherwise manipulate the medical device 2402 to facilitate achieving the objective. For example, the reference manipulation overlay 2404 may indicate how a user should hold, orient, or otherwise manipulate a medical device, such as an infusion device or a serter, with respect to an infusion set (e.g., infusion set 225), or vice versa, when configuring the infusion set for operation.

Referring again to FIG. 23, in the illustrated embodiment, the device training process 2300 continues by detecting or otherwise identifying the current state of the user's manipulation with the medical device (task 2308). In this regard, based on the analysis of the image(s) from the imaging device 808, the control module 802 identifies or otherwise determines the current position and/or orientation of the user's hands and/or fingers relative to the medical device 702. Thereafter, the device training process 2300 generates or otherwise provides feedback information based on the observed state of the user's manipulation of the medical device relative to the reference manipulation (task 2310). For example, in some embodiments, the control module 802 calculates or otherwise determines a difference or deviation between the observed state of the user's hands and/or finders and the reference manipulation corresponding to the reference manipulation overlay 2404, and then generates or otherwise provides a guidance overlay that indicates, to the user, how he or she should adjust his or her hands and/or finders to reduce the difference and better align with the reference manipulation. In some embodiments, the control module 802 calculates or otherwise determines a score or other metric that quantifies the user's performance based on the difference or deviation between the observed state of the user's hands and/or finders and the reference manipulation. The control module 802 may generate or otherwise provide an overlay that indicates, to the user, his or her score with respect to performing the necessary manipulation of the medical device to achieve the intended objective. In some embodiments, the score or other quantitative metrics associated with the user may be stored or otherwise maintained and analyzed to determine whether or not to certify the user with respect to performing a particular manipulation of the medical device. For example, the device training process 2300 may be utilized to determine when to certify an individual user once his or her score with respect to a particular manipulation is above a threshold score, or the individual user has successively achieved scores above the threshold over a successive number of device manipulations.

The loop defined by tasks 2302, 2304, 2306, 2308 and 2310 may repeat to walk the user through a sequence of manipulations or interactions with the medical device until achieving the desired objective. For example, a user may be sequentially shown how to specifically orient or manipulate his or her hands to remove a sensor from its packaging and thereafter how to hold the sensor and/or an insertion device with his or her hands throughout the steps required to assemble the sensor with the insertion device. In some embodiments, the user may be scored or otherwise have his or her performance quantified with respect to individual steps in a sequence of manipulations, while also being scored across the entire sequence of manipulations (e.g., by averaging the scores for individual steps, determining a cumulative score as a weighted sum of the scores for the individual steps, etc.). Thus, augmented reality may be utilized to train patients or other users for achieving different objectives with respect to a medical device. Additionally, the amount of time required for a patient or user to perform individual steps may be recorded and analyzed (e.g., for purposes of compliance with training and/or reimbursement requirements, facilitating redesign or simplification of processes, and/or the like).

Patient Gamification Using Augmented Reality

Figure 25:
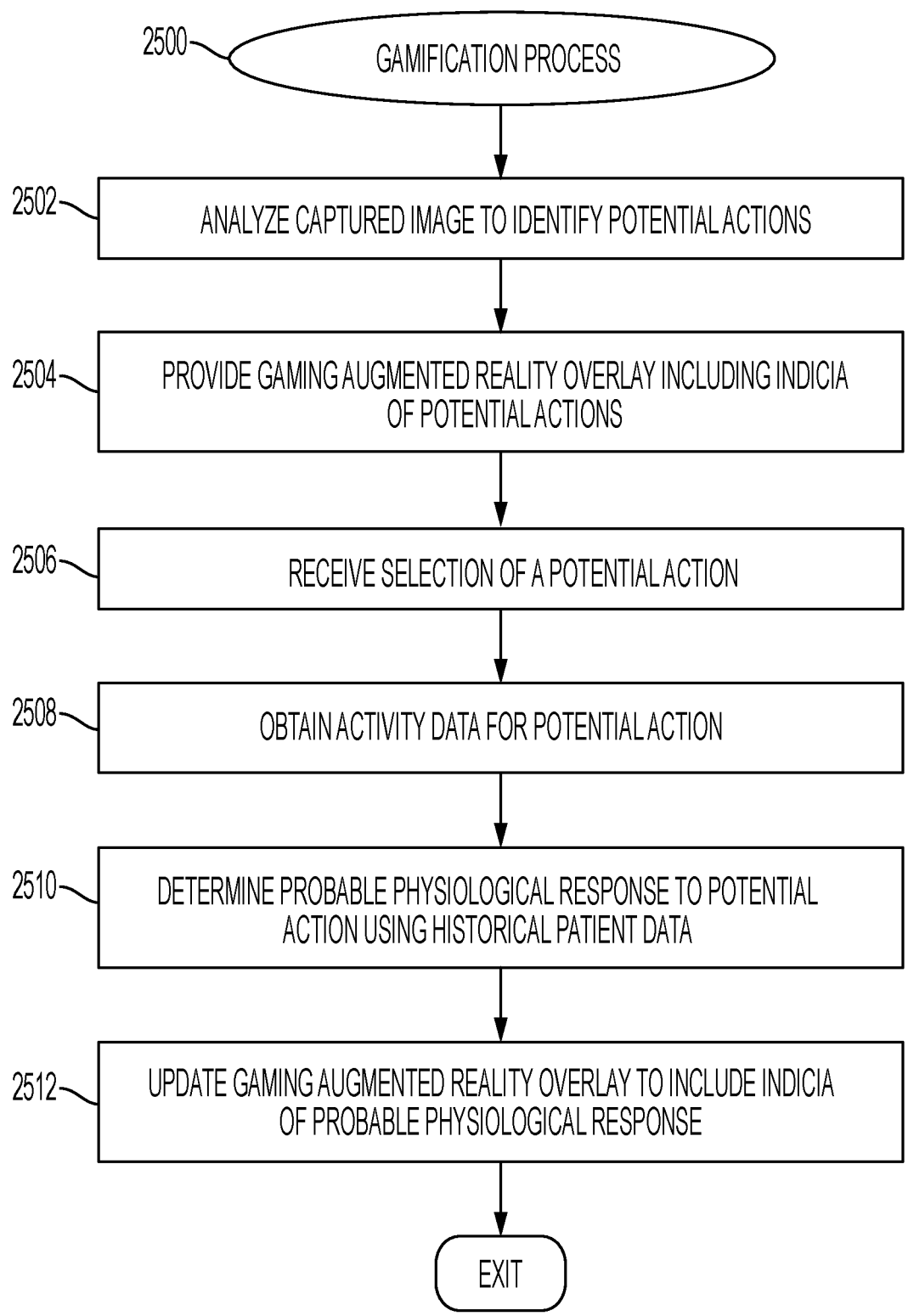
FIG. 25 is a flow diagram of an exemplary gamification process in one or more exemplary embodiments.

Referring now to FIG. 25, in one or more exemplary embodiments, augmented reality may also be utilized to incorporate visual overlays pertaining to video game simulations. For example, as described above, historical data associated with the patient may be utilized to generate models for calculating the probable physiological response by the patient to different combinations of daily activities or actions. In this regard, a virtual player character representative of an individual patient to be used in a video game simulation may be generated based on the patient's historical data, for example, by mapping the patient's historical or probable physiological responses to a set of attributes for that player character. Thereafter, captured images may be analyzed or otherwise processed to identify potential actions or activities that could be undertaken by the virtual player character given the patient's current environment. An overlay identifying the potential actions may be depicted overlying the environment using augmented reality, and the patient may interact with the overlay to select or otherwise identify actions for the virtual player character. A probable physiological response by the virtual player character to the selected actions may be calculated based at least in part on attributes assigned to the virtual player character and/or the relationships between activity data for the selected action(s) and the historical data associated with the patient. A graphical indication of the probable physiological response by the virtual player character within the video game simulation may then be generated or otherwise provided overlying the surrounding environment using augmented reality.

The various tasks performed in connection with the gamification process 2500 may be performed by hardware, firmware, software executed by processing circuitry, or any combination thereof. For illustrative purposes, the following description refers to elements mentioned above in connection with FIGS. 1-8. For purposes of explanation, the gamification process 2500 may be described herein primarily in the context of being implemented at a client device 706, 800 in a patient management system 700. It should be appreciated that the gamification process 2500 may include any number of additional or alternative tasks, the tasks need not be performed in the illustrated order and/or the tasks may be performed concurrently, and/or the gamification process 2500 may be incorporated into a more comprehensive procedure or process having additional functionality not described in detail herein. Moreover, one or more of the tasks shown and described in the context of FIG. 25 could be omitted from a practical embodiment of the gamification process 2500 as long as the intended overall functionality remains intact.

The illustrated gamification process 2500 begins by analyzing or otherwise processing captured images to identify potential actions that could be undertaken by the virtual player character representative of the patient from within the environment surrounding the patient (task 2502). For example, based on the analysis of the image(s) from the imaging device 808, the control module 802 may identify or otherwise detect food, beverages, or other consumable items (or indicia thereof), items or other indicia associated with exercise (e.g., a treadmill, a gym, or the like), or other items or indicia associated with different potential behaviors (e.g., sleep, stress, or the like) that could influence the patient's physiological condition. Thereafter, the gamification process 2500 generates or otherwise provides one or more graphical overlays that include indicia of the potential action(s) identified based on the surrounding environment (task 2504). For example, the control module 802 may generate a gaming augmented reality GUI display including selectable GUI elements corresponding to the potential actions that are presented overlying the surrounding environment and disposed adjacent to or otherwise in vicinity of the portions of the surrounding environment where the potential actions were identified. The patient may then concurrently analyze the selectable GUI elements with respect to the surrounding environment and determine which potential actions that the patient would like to have the virtual player character engage in.

The gamification process 2500 continues by receiving or otherwise identifying selection of a potential action and obtaining activity data pertaining to the potential action (tasks 2506, 2508). For example, the patient may select an overlaid GUI element from within the gaming augmented reality GUI display to indicate the potential action to be undertaken by the virtual player character. In some embodiments, the patient may also input or otherwise provide data or information quantifying or otherwise characterizing the nature of the action to be engaged in (e.g., an amount of carbohydrates, a duration or intensity of exercise, and/or the like). In other embodiments, the historical activity data associated with the patient may be analyzed to identify probable characteristics associated with the action. Based on the probable characteristics for the selected action, the gamification process 2500 calculates or otherwise determines a probable physiological response to the action by the virtual player character and then updates the gaming overlay to provide indicia of the probable physiological response (tasks 2510, 2512). For example, the probable or assigned characteristics for the selected action may be provided as input to a physiological model for the patient using other attributes or data associated with the patient's virtual player character to calculate the probable physiological response to the selected action. An overlay may then be provided within the gaming augmented reality GUI display that indicates the probable physiological response to the selected action by the virtual player character (e.g., a net change in glucose level, percentage time in range, and/or the like). In this manner, the gamification process 2500 may provide the patient with a greater understanding of his or her likely physiological response to different actions or sequences thereof.

It should be noted that the gamification process 2500 may also be implemented or incorporated with the various augmented reality GUI displays described above to allow the patient to effectively simulate different potential actions using the virtual player character. For example, if the patient is interested in deviating from guidance provided above in connection with the proactive guidance process 1800 of FIG. 18, the patient may modify the characteristics or other activity data associated with a potential action to ascertain the probable physiological response by the patient's representative virtual player character, and thereby understand how the patient's own physiological condition is likely to be affected if the patient were to deviate from the guidance in the desired manner.

For the sake of brevity, conventional techniques related to glucose sensing and/or monitoring, bolusing, closed-loop glucose control, patient modeling, augmented reality, image processing, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A non-transitory computer-readable medium having instructions stored thereon that, when executed by a processor, cause the processor to:
   analyze one or more images captured by an imaging device to identify image content indicative of a meal capable of influencing a physiological condition of a patient; and
   in response to identifying the meal based at least in part on the one or more images:
   determine nutritional information for the meal based at least in part on the one or more images; and
   automatically adjust one or more closed-loop control parameters of a medical device based at least in part on the nutritional information to account for a predicted postprandial glycemic response based on the nutritional information for the meal, resulting in one or more adjusted closed-loop control parameters, wherein the medical device is configured to deliver a fluid to the patient in accordance with the one or more adjusted closed-loop control parameters.

2. The computer-readable medium of claim 1, wherein the instructions cause the processor to provide the one or more adjusted closed-loop control parameters to the medical device via a network.

3. The computer-readable medium of claim 1, wherein the instructions cause the processor to determine an increased bolus dosage amount of the fluid for delivery by the medical device by scaling a carbohydrate ratio when the nutritional information comprises more carbohydrates relative to an amount of fat.

4. The computer-readable medium of claim 1, wherein the instructions cause the processor to command a closed-loop control system of the medical device to temporarily suspend delivery of the fluid when the nutritional information comprises more carbohydrates relative to an amount of fat.

5. The computer-readable medium of claim 1, wherein the instructions cause the processor to determine a decreased bolus dosage amount of the fluid for delivery by the medical device by scaling a carbohydrate ratio when the nutritional information comprises more fat relative to an amount of carbohydrates.

6. The computer-readable medium of claim 1, wherein the instructions cause the processor to command a closed-loop control system of the medical device to utilize a lower target glucose value to temporarily increase delivery of the fluid by the closed-loop control system of the medical device when the nutritional information comprises more fat relative to an amount of carbohydrates.

7. The computer-readable medium of claim 1, wherein the instructions cause the processor to provide an overlay including a graphical indication of the one or more adjusted closed-loop control parameters on a display associated with an electronic device including the imaging device.

8. The computer-readable medium of claim 1, wherein the instructions cause the processor to command a control system of the medical device to dynamically adjust delivery of the fluid based on one or more subsequent images captured by the imaging device.

9. The computer-readable medium of claim 1, the nutritional information comprising an expected amount of carbohydrates, wherein the instructions cause the processor to:
determine a consumed amount of carbohydrates based on one or more subsequent images captured by the imaging device; and
command a control system of the medical device to dynamically adjust delivery of the fluid based on a difference between the expected amount of carbohydrates and the consumed amount of carbohydrates.

10. The computer-readable medium of claim 1, wherein the instructions cause the processor to determine an adjusted bolus dosage amount based on the nutritional information.

11. The computer-readable medium of claim 1, wherein the instructions cause the processor to determine an adjusted bolus delivery schedule based on the nutritional information.

12. The computer-readable medium of claim 1, wherein:
the one or more adjusted closed-loop control parameters comprise an adjusted gain coefficient; and
the medical device autonomously delivers the fluid to the patient based at least in part on a difference between a current measurement of the physiological condition and a target value for the physiological condition using the adjusted gain coefficient.

13. The computer-readable medium of claim 1, wherein the one or more adjusted closed-loop control parameters tune responsiveness of a closed-loop control system of the medical device to deviations between a current measurement of the physiological condition and a target value for the physiological condition.

14. The computer-readable medium of claim 1, wherein the instructions cause the processor to automatically adjust the one or more closed-loop control parameters by increasing at least one of a minimum basal rate setting and a maximum basal rate setting during a postprandial period.

15. The computer-readable medium of claim 1, wherein:
the one or more adjusted closed-loop control parameters comprise an adjusted target value for the physiological condition; and
the medical device autonomously delivers the fluid to the patient based at least in part on a difference between a current measurement of the physiological condition and the adjusted target value.

16. The computer-readable medium of claim 15, wherein the instructions cause the processor to automatically decreasing a target value for the physiological condition in advance of the meal resulting in the adjusted target value to achieve an increased infusion rate.

17. An electronic device comprising:
an imaging device;
a data storage element having executable instructions stored thereon; and
a processor coupled to the imaging and the data storage element, wherein the executable instructions cause the processor to:
analyze one or more images captured by the imaging device to identify image content indicative of a meal capable of influencing a physiological condition of a patient; and
in response to identifying the meal based at least in part on the one or more images:
determine nutritional information for the meal based at least in part on the one or more images; and
automatically adjust one or more closed-loop control parameters of a medical device based at least in part on the nutritional information to account for a predicted postprandial glycemic response based on the nutritional information for the meal, resulting in one or more adjusted closed-loop control parameters, wherein the medical device delivers a fluid to the patient in accordance with the one or more adjusted closed-loop control parameters.

18. The electronic device of claim 17, further comprising a display coupled to the processor, wherein the instructions cause the processor to display an augmented reality graphical user interface (GUI) display including a graphical indication of the one or more adjusted closed-loop control parameters on the display.

19. A method of operating a medical device capable of delivering a fluid to a patient, the fluid influencing a physiological condition of the patient, the method comprising:
analyzing one or more images captured by an imaging device to identify image content indicative of a meal capable of influencing the physiological condition of the patient; and
in response to identifying the meal based at least in part on the one or more images:
determining, by a control system of an electronic device including the imaging device, nutritional information for the meal based at least in part on the one or more images; and
automatically adjusting, by the control system, one or more closed-loop control parameters of the medical device based at least in part on the nutritional information to account for a predicted postprandial glycemic response based on the nutritional information for the meal, resulting in one or more adjusted closed-loop control parameters, wherein the medical device autonomously delivers the fluid to the patient in accordance with the one or more adjusted closed-loop control parameters.

20. The method of claim 19, further comprising providing the one or more adjusted closed-loop control parameters to the medical device via a network.

* * * * *